United States Patent [19]
Magagnin et al.

[11] Patent Number: 6,107,069
[45] Date of Patent: Aug. 22, 2000

[54] RECOMBINANT KYNURENINE-3-HYDROXYLASE ENZYME AND PROCESS FOR ITS PREPARATION

[75] Inventors: Simona Magagnin; Luca Benatti; Massimo Cini; Carmela Speciale; Nevie Covini, all of Milan, Italy

[73] Assignee: Pharmacia & Upjohn S.p.A., Milan, Italy

[21] Appl. No.: 09/147,522

[22] PCT Filed: Jul. 3, 1997

[86] PCT No.: PCT/EP97/03589

§ 371 Date: Jan. 14, 1999

§ 102(e) Date: Jan. 14, 1999

[87] PCT Pub. No.: WO98/02553

PCT Pub. Date: Jan. 22, 1998

[30] Foreign Application Priority Data

Jul. 15, 1996 [GB] United Kingdom ............... 9614823

[51] Int. Cl.[7] .............................. C12N 9/02; C12N 1/21; C12N 15/53; C12N 1/19; C07H 21/04

[52] U.S. Cl. ............... 435/189; 435/252.3; 435/254.2; 435/320.1; 435/325; 435/348; 536/23.2; 536/23.5

[58] Field of Search .................. 435/189, 252.3, 435/254.2, 320.1, 325, 348; 536/23.2, 23.5

[56] References Cited

PUBLICATIONS

Warren et al. (May 31, 1996) Genetica, vol. 98, pp. 249–262.
Sigel (1990) J. Membrane Biol., vol. 117, pp. 201–221.
Nishimoto et al. (1979) J. Chromatography, vol. 169, pp. 357–364 (abstract).

*Primary Examiner*—Elizabeth Slobodyansky
*Attorney, Agent, or Firm*—Oblon, Spivak, McClelland, Maier & Naustadt, P.C.

[57] ABSTRACT

The present invention provides an isolated polynucleotide encoding for the kynurenine-3-hydrolase (Kyn-3-OHase) and methods of transiently expressing thereof.

24 Claims, 9 Drawing Sheets

```
rat Kyn-3-Hase   MASSDTEGKR  WVV[GGgLVG  A]NACFLA]R  NFQWDVMEAR  EDIRVANFM-  RG-RSINLAL  SYRGQALKA  VGLE-     72
YBJ8_YEAST       MSBS------  VAI[GAGLVG  C]AALAFSKE  GYNVTLMDFR  QDPRLDTTKN  KNLKSINLAI  SARGIDALKS IDPDA     69 rat Kyn-3-Hase   -DQIVSKGVP  MKARMIHSLS  GKKSAIPYGN  KSQYILSISR  EKLNKDLITA  VESYPNAKVH  FGHKLSKC---  CPEEG   144
YBJ8_YEAST       CEHILQDMIP  MKGRMIHDLK  GRQESQLYGL  HGEAINSINR  SVLNNSLLDE  LEK-STTELK  FGHKLVKIEW  TDDKQ    143 rat Kyn-3-Hase   I--LTMLGPN  KVPRDITCDL  IVGCDGAYST  VRAHLMKKPR  FDYSGQYIPH  GVMELIIPPK  N------GE  YAMEP     210
YBJ8_YEAST       ICHFAIGEDL  KIPHTEKYDF  VIGCDGAYSA  TRSQMQRKVE  MDFSGEYMNL  RYIELYIPPT  EEFKPNYGGN  FAIAP    218 rat Kyn-3-Hase   NCLHIWPRNA  FMMIALPNMD  KIFTCILFMS  FEEFEKLPTH  SDVLDFFQKN  FPDAIPLMGE  QALMRDFFL-  ----     279
YBJ8_YEAST       DHLHIWPRHK  FMLIALANSD  GSFISTEFGS  KDQISDLIT-  ----------  -------S  KSRVREFLIE  NFPDI     273 rat Kyn-3-Hase   ---------  ------PAQP  MISVRDSPFH  LK-SRCVLMG  DAAHAIVPFF  GQGMNAGFED  CLVFDELMDK  FNND]    338
YBJ8_YEAST       INIMDLDDAV  KRFITYPKES  LVCVNDKPYD  VPGGKAILLG  DAAHAMVPFY  GQGMNLGFED  VRILMALLKK  HSGDR    348 rat Kyn-3-Hase   SVCLPEFSRF  RIPDDHAISD  LSMYNYIEMR  QRLLDKFLHA  LMPSTFFPLY  TMVAFTRIRY  HEAVL             413
YBJ8_YEAST       GRAFTEYTQT  RHKDLVSITE  LAKRNYKEMS  HDVISKRFLL  RKKLDALFSI  IMKDKWIPLY  TMISFRSDIS  YSRAL    423 rat Kyn-3-Hase   RWHWQKKVIN  RGLFVLGSLV  AIGSAYILVH  HLSPRPLEIL  RSAWTGTSGH  WNRSADISPR  VPWSH              478
YBJ8_YEAST       ERA-GKQ---T  RILKRLESL-  TLGMLSIGGY  KL-------  --FKFL----  -----T  RERS-----            460
```

FIG. 1

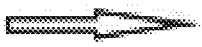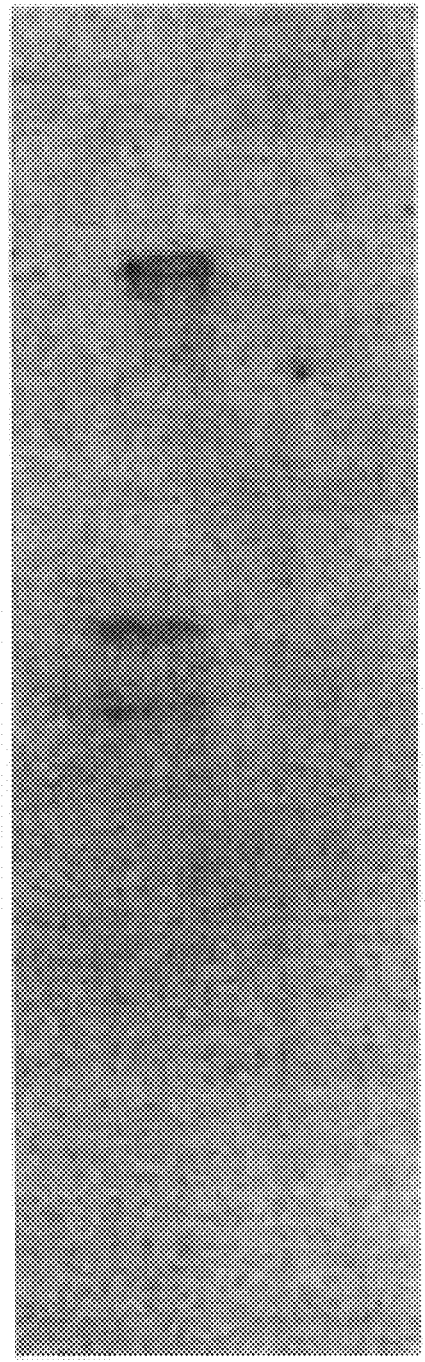
FIG.3

```
  1  ............GCACAGATAATTGTGAAAAATACTTCAGCAGTTATGG  37
                 |||    ||||||||||||||||||||||||||||||
  1  GGCACGAGCAGAAGCAACAATAATTGTGAAAAATACTTCAGCAGTTATGG  50

38  ACTCATCTGTCATTCAAAGGAAAAAAGTAGCTGTCATTGGTGGTGGCTTG  87
     ||||||||||||||||||||||||||||||||||||||||||||||||||
 51  ACTCATCTGTCATTCAAAGGAAAAAAGTAGCTGTCATTGGTGGTGGCTTG 100

88  GTTGGCTCATTACAAGCATGCTTTCTTGCAAAGAGGAATTTCCAGATTGA 137
     ||||||||||||||||||||||||||||||||||||||||||||||||||
101  GTTGGCTCATTACAAGCATGCTTTCTTGCAAAGAGGAATTTCCAGATTGA 150

138  TGTATATGAAGCTAGGGAAGATACTCGAGTGGCTACCTTCACACGTGGAA 187
     ||||||||||||||||||||||||||||||||||||||||||||||||||
151  TGTATATGAAGCTAGGGAAGATACTCGAGTGGCTACCTTCACACGTGGAA 200

188  GAAGCATTAACTTAGCCCTTTCTCATAGAGGACGACAAGCCTTGAAAGCT 237
     ||||||||||||||||||||||||||||||||||||||||||||||||||
201  GAAGCATTAACTTAGCCCTTTCTCATAGAGGACGACAAGCCTTGAAAGCT 250

238  GTTGGCCTGGAAGATCAGATTGTATCCCAAGGTATTCCCATGAGAGCAAG 287
     ||||||||||||||||||||||||||||||||||||||||||||||||||
251  GTTGGCCTGGAAGATCAGATTGTATCCCAAGGTATTCCCATGAGAGCAAG 300

288  AATGATCCACTCTCTTTCAGGAAAAAAGTCTGCAATTCCCTATGGGACAA 337
     ||||||||||||||||||||||||||||||||||||||||||||||||||
301  AATGATCCACTCTCTTTCAGGAAAAAAGTCTGCAATTCCCTATGGGACAA 350

338  AGTCTCAGTATATTCTTTCTGTAAGCAGAGAAAATCTAAACAAGGATCTA 387
     ||||||||||||||||||||||||||||||||||||||||||||||||||
351  AGTCTCAGTATATTCTTTCTGTAAGCAGAGAAAATCTAAACAAGGATCTA 400

388  TTGACTGCTGCTGAGAAATACCCCAATGTGAAAATGCACTTTAACCACAG 437
     ||||||||||||||||||||||||||||||||||||||||||||||||||
401  TTGACTGCTGCTGAGAAATACCCCAATGTGAAAATGCACTTTAACCACAG 450

438  GCTGTTGAAATGTAATCCAGAGGAAGGAATGATCACAGTGCTTGGATCTG 487
     ||||||||||||||||||||||||||||||||||||||||||||||||||
451  GCTGTTGAAATGTAATCCAGAGGAAGGAATGATCACAGTGCTTGGATCTG 500
```

*FIG. 4A*

```
488  ACAAAGTTCCCAAAGATGTCACTTGTGACCTCATTGTAGGATGTGATGGA  537
     ||||||||||||||||||||||||||||||||||||||||||||||||||
501  ACAAAGTTCCCAAAGATGTCACTTGTGACCTCATTGTAGGATGTGATGGA  550

538  GCCTATTCAACTGTCAGATCTCACCTGATGAAGAAACCTCGCTTTGATTA  587
     ||||||||||||||||||||||||||||||||||||||||||||||||||
551  GCCTATTCAACTGTCAGATCTCACCTGATGAAGAAACCTCGCTTTGATTA  600

588  CAGTCAGCAGTACATTCCTCATGGGTACATGGAGTTGACTATTCCACCTA  637
     ||||||||||||||||||||||||||||||||||||||||||||||||||
601  CAGTCAGCAGTACATTCCTCATGGGTACATGGAGTTGACTATTCCACCTA  650

638  AGAACGGAGATTATGCCATGGAACCTAATTATCTGCATATTTGGCCTAGA  687
     ||||||||||||||||||||||||||||||||||||||||||||||||||
651  AGAACGGAGATTATGCCATGGAACCTAATTATCTGCATATTTGGCCTAGA  700

688  AATACCTTTATGATGATTGCACTTCCTAACATGAACAAATCATTCACATG  737
     ||||||||||||||||||||||||||||||||||||||||||||||||||
701  AATACCTTTATGATGATTGCACTTCCTAACATGAACAAATCATTCACATG  750

738  TACTTTGTTCATGCCCTTTGAAGAGTTTGAAAAACTTCTAACCAGTAATG  787
     ||||||||||||||||||||||||||||||||||||||||||||||||||
751  TACTTTGTTCATGCCCTTTGAAGAGTTTGAAAAACTTCTAACCAGTAATG  800

788  ATGTGGTAGATTTCTTCCAGAAATACTTTCCGGATGCCATCCCTCTAATT  837
     ||||||||||||||||||||||||||||||||||||||||||||||||||
801  ATGTGGTAGATTTCTTCCAGAAATACTTTCCGGATGCCATCCCTCTAATT  850

838  GGAGAGAAACTCCTAGTGCAAGATTTCTTCCTGTTGCCTGCCCAGCCCAT  887
     ||||||||||||||||||||||||||||||||||||||||||||||||||
851  GGAGAGAAACTCCTAGTGCAAGATTTCTTCCTGTTGCCTGCCCAGCCCAT  900

888  GATATCTGTAAAGTGCTCTTCATTTCACTTTAAATCTCACTGTGTACTGC  937
     ||||||||||||||||||||||||||||||||||||||||||||||||||
901  GATATCTGTAAAGTGCTCTTCATTTCACTTTAAATCTCACTGTGTACTGC  950

938  TGGGAGATGCAGCTCATGCTATAGTGCCGTTTTTTGGGCAAGGAATGAAT  987
     ||||||||||||||||||||||||||||||||||||||||||||||||||
951  TGGGAGATGCAGCTCATGCTATAGTGCCGTTTTTTGGGCAAGGAATGAAT  1000
```

*FIG. 4B*

```
 988 GCGGGCTTTGAAGACTGCTTGGTATTTGATGAGTTAATGGATAAATTCAG 1037
     ||||||||||||||||||||||||||||||||||||||||||||||||||
1001 GCGGGCTTTGAAGACTGCTTGGTATTTGATGAGTTAATGGATAAATTCAG 1050

1038 TAACGACCTTAGTTTGTGTCTTCCTGTGTTCTCAAGATTGAGAATCCCAG 1087
     ||||||||||||||||||||||||||||||||||||||||||||||||||
1051 TAACGACCTTAGTTTGTGTCTTCCTGTGTTCTCAAGATTGAGAATCCCAG 1100

1088 ATGATCACGCGATTTCAGACCTATCCATGTACAATTACATAGAGATGCGA 1137
     ||||||||||||||||||||||||||||||||||||||||||||||||||
1101 ATGATCACGCGATTTCAGACCTATCCATGTACAATTACATAGAGATGCGA 1150

1138 GCACATGTCAACTCAAGCTGGTTCATTTTTCAGAAGAACATGGAGAGATT 1187
     ||||||||||||||||||||||||||||||||||||||||||||||||||
1151 GCACATGTCAACTCAAGCTGGTTCATTTTTCAGAAGAACATGGAGAGATT 1200

1188 TCTTCATGCGATTATGCCATCGACCTTTATCCCTCTCTATACAATGGTCA 1237
     ||||||||||||||||||||||||||||||||||||||||||||||||||
1201 TCTTCATGCGATTATGCCATCGACCTTTATCCCTCTCTATACAATGGTCA 1250

1238 CTTTTTCCAGAATAAGATACCATGAGGCTGTGCAGCGTTGGCATTGGCAA 1287
     ||||||||||||||||||||||||||||||||||||||||||||||||||
1251 CTTTTTCCAGAATAAGATACCATGAGGCTGTGCAGCGTTGGCATTGGCAA 1300

1288 AAAAAGGTGATAAACAAAGGACTCTTTTTCTTGGGATCACTGATAGCCAT 1337
     ||||||||||||||||||||||||||||||||||||||||||||||||||
1301 AAAAAGGTGATAAACAAAGGACTCTTTTTCTTGGGATCACTGATAGCCAT 1350

1338 CAGCAGTACCTACCTACTTATACACTACATGTCACCACGATCTTTCCTCT 1387
     ||||||||||||||||||||||||||||||||||||||||||||||||||
1351 CAGCAGTACCTACCTACTTATACACTACATGTCACCACGATCTTTCCTCT 1400

1388 GCTTGAGAAGACCATGGAACTGGATAGCTCACTTCCGGAATACAACATGT 1437
     ||||||||||||||||||||||||||||||||||||||||||||||||||
1401 GCTTGAGAAGACCATGGAACTGGATAGCTCACTTCCGGAATACAACATGT 1450

1438 TTCCCCGCAAAGGCCGTGGACTCCCTAGAACAAATTTCCAATCTCATTAG 1487
     ||||||||||||||||||||||||||||||||||||||||||||||||||
1451 TTCCCCGCAAAGGCCGTGGACTCCCTAGAACAAATTTCCAATCTCATTAG 1500
```

*FIG. 4C*

```
1488  CAGGTGATAGAAAGGTTTTGTGGTAGCAAATGCATGATTTCTCTGTGACC  1537
      ||||||||||||||||||||||||||||||||||||||||||||||||||
1501  CAGGTGATAGAAAGGTTTTGTGGTAGCAAATGCATGATTTCTCTGTGACC  1550

1538  AAAATTAAGCATGAAAAAAATGTTTCCATTGCCATATTTGATTCACTAGT  1587
      ||||||||||||||||||||||||||||||||||||||||||||||||||
1551  AAAATTAAGCATGAAAAAAATGTTTCCATTGCCATATTTGATTCACTAGT  1600

1588  GGAAGATAGTGTTCTGCTTATAATTAAACTGAATGTAGAGT.........  1628
      |||||||||||||||||||||||||||||||||||||||||
1601  GGAAGATAGTGTTCTGCTTATAATTAAACTGAATGTAGAGTATCTCTGTA  1650
```

*FIG. 4D*

```
ratK3DH    1    MASSDTEGKRVVVIGGGLVGALNACFLAKRNFQVDVYEAREDIRVANFMR    50
                |.||.: |:|.||||||||.|.||||||||||: |||||||||.|||.||
humK3DH    1    MDSSVIQRKKVAVIGGGLVGSLQACFLAKRNFQIDVYEAREDTRVATFTR    50 ratK3DH   51    GRSINLALSYRGRQALKAVGLEDQIVSKGVPMKARMIHSLSGKKSAIPYG   100
                ||||||||. ||||||||||||||||. |: ||: |||||||||||||||
humK3DH   51    GRSINLALSHRGRQALKAVGLEDQIVSQGIPMRARMIHSLSGKKSAIPYG   100 ratK3DH  101    NKSQYILSISREKLNKDLLTAVESYPNAKVHFGHKLSKCCPEEGILTMLG   150
                .|||||||:|||.||||||||.|.|||.|:||.|:||||||::|:|||
humK3DH  101    TKSQYILSVSRENLNKDLLTAAEKYPNVKMHFNHRLLKCNPEEGMITVLG   150 ratK3DH  151    PNKVPRDITCDLIVGCDGAYSTVRAHLMKKPRFDYSQQYIPHGYMELTIP   200
                .:|||:|:||||||||||||||||.|||||||||||||||||||||||||
humK3DH  151    SDKVPKDVTCDLIVGCDGAYSTVRSHLMKKPRFDYSQQYIPHGYMELTIP   200 ratK3DH  201    PKNGEYAMEPNCLHIWPRNAFMMIALPNMDKTFTCTLFMSFEEFEKLPTH   250
                ||||:||||||:|||||||.|||||||||||:|.|||||||.|||||||||  |
humK3DH  201    PKNGDYAMEPNYLHIWPRNTFMMIALPNMNKSFTCTLFMPFEEFEKLLTS   250 ratK3DH  251    SDVLDFFQKNFPDAIPLMGEQALMRDFFLLPAQPMISVKCSPFHLKSRCV   300
                .||:||||| ||||||:||. |:.||||||||||||||||.||:||:||
humK3DH  251    NDVVDFFQKYFPDAIPLIGEKLLVQDFFLLPAQPMISVKCSSFHFKSHCV   300 ratK3DH  301    LMGDAAHAIVPFFGQGMNAGFEDCLVFDELMDKFNNDLSVCLPEFSRFRI   350
                |:||||||||||||||||||||||||||||||||.||||:|||  |||:||
humK3DH  301    LLGDAAHAIVPFFGQGMNAGFEDCLVFDELMDKFSNDLSLCLPVFSRLRI   350
```

*FIG. 5A*

```
ratK3OH   351  PDDHAISDLSMYNYIEMRAHVNSRWFLFQRLLDKFLHALMPSTFIPLYTM  400
               ||||||||||||||||||||||||.||:||:  :::||||:||||||||||||
humK3OH   351  PDDHAISDLSMYNYIEMRAHVNSSWFIFQKNMERFLHAIMPSTFIPLYTM  400 ratK3OH   401  VAFTRIRYHEAVLRWHWQKKVINRGLFVLGSLVAIGSAYILVHHLSPRPL  450
               |.|.|||||||| |||||||||:|||.||||:||:|.|:|:|.:|||.:
humK3OH   401  VTFSRIRYHEAVQRWHWQKKVINKGLFFLGSLIAISSTYLLIHYMSPRSF  450 ratK3OH   451  ELLRSAWTGTSGHWNRS..........ADISPRVPWSH   478
                ||.:|. ..  :|.            .:||  :,:
humK3OH   451  LCLRRPWNWIAHFRNTTCFPAKAVDSLEQISNLISR..  486
```

*FIG. 5B*

SEQUENCE LISTING

<160> NUMBER OF SEQ ID NOS: 9

<210> SEQ ID NO 1
<211> LENGTH: 1733
<212> TYPE: DNA
<213> ORGANISM: Rattus rattus
<220> FEATURE:
<221> NAME/KEY: CDS
<222> LOCATION: (45)..(1481)

<400> SEQUENCE: 1

```
ccacgcgtcc gagctcctac ctgagcagag gtattctggc agca atg gca tcg tcg         56
                                              Met Ala Ser Ser
                                                1 gac act gaa gga aaa aga gtg gtt gtt atc ggt ggt ggt ttg gtt gga       104
Asp Thr Glu Gly Lys Arg Val Val Val Ile Gly Gly Gly Leu Val Gly
  5                  10                  15                  20 gca ttg aac gcg tgc ttt ctc gca aag agg aat ttc caa gtt gat gtg       152
Ala Leu Asn Ala Cys Phe Leu Ala Lys Arg Asn Phe Gln Val Asp Val
              25                  30                  35
```

-continued

| | | |
|---|---|---|
| tac gaa gct agg gaa gat att cga gtg gct aac ttt atg cgt gga aga<br>Tyr Glu Ala Arg Glu Asp Ile Arg Val Ala Asn Phe Met Arg Gly Arg<br>                   40                          45                 50 | 200 |
| agc att aat ttg gcc ctt tct tat aga gga cgg cag gcc ttg aag gcc<br>Ser Ile Asn Leu Ala Leu Ser Tyr Arg Gly Arg Gln Ala Leu Lys Ala<br>        55                       60                       65 | 248 |
| gtt ggt ctg gaa gat cag atc gtg tcc aaa ggt gtg ccc atg aaa gcc<br>Val Gly Leu Glu Asp Gln Ile Val Ser Lys Gly Val Pro Met Lys Ala<br> 70                         75                       80 | 296 |
| aga atg atc cac tct ctc tcg gga aag aag tct gca att ccc tat ggg<br>Arg Met Ile His Ser Leu Ser Gly Lys Lys Ser Ala Ile Pro Tyr Gly<br> 85                         90                       95              100 | 344 |
| aac aag tca cag tat atc ctt tca ata agc aga gaa aag tta aac aag<br>Asn Lys Ser Gln Tyr Ile Leu Ser Ile Ser Arg Glu Lys Leu Asn Lys<br>               105                    110                115 | 392 |
| gat ctg ctg act gcc gtg gag tcc tac ccc aat gca aag gtg cac ttt<br>Asp Leu Leu Thr Ala Val Glu Ser Tyr Pro Asn Ala Lys Val His Phe<br>             120                      125                    130 | 440 |
| ggc cac aag ctg tca aaa tgc tgt ccg gag gaa ggg ata ctc acg atg<br>Gly His Lys Leu Ser Lys Cys Cys Pro Glu Glu Gly Ile Leu Thr Met<br>            135                    140                   145 | 488 |
| ctt gga ccc aac aaa gtt ccc aga gac atc acg tgt gac ctc att gta<br>Leu Gly Pro Asn Lys Val Pro Arg Asp Ile Thr Cys Asp Leu Ile Val<br>150                       155                      160 | 536 |
| gga tgt gat ggg gcc tac tca act gtc aga gct cac ctc atg aag aag<br>Gly Cys Asp Gly Ala Tyr Ser Thr Val Arg Ala His Leu Met Lys Lys<br>165                      170                    175                180 | 584 |
| ccc cgt ttt gat tac agt cag caa tat atc cct cat ggc tat atg gag<br>Pro Arg Phe Asp Tyr Ser Gln Gln Tyr Ile Pro His Gly Tyr Met Glu<br>             185                      190                    195 | 632 |
| ctg aca att cca cct aag aac ggg gag tat gcc atg gaa cct aac tgt<br>Leu Thr Ile Pro Pro Lys Asn Gly Glu Tyr Ala Met Glu Pro Asn Cys<br>             200                      205                    210 | 680 |
| ctt cac att tgg cct aga aat gcc ttt atg atg atc gcc cta ccg aac<br>Leu His Ile Trp Pro Arg Asn Ala Phe Met Met Ile Ala Leu Pro Asn<br>             215                      220                    225 | 728 |
| atg gac aaa tct ttc aca tgc acc ttg ttc atg tcc ttt gag gag ttt<br>Met Asp Lys Ser Phe Thr Cys Thr Leu Phe Met Ser Phe Glu Glu Phe<br>230                       235                      240 | 776 |
| gaa aag ctt cca acg cat agt gat gtg ctg gac ttc ttc cag aag aac<br>Glu Lys Leu Pro Thr His Ser Asp Val Leu Asp Phe Phe Gln Lys Asn<br>245                       250                    255                260 | 824 |
| ttt cca gat gcc atc cct ctg atg ggc gag caa gcc ctc atg aga gat<br>Phe Pro Asp Ala Ile Pro Leu Met Gly Glu Gln Ala Leu Met Arg Asp<br>             265                      270                    275 | 872 |
| ttc ttt ctg ttg cct gcc cag ccc atg ata tca gta aag tgc tct ccc<br>Phe Phe Leu Leu Pro Ala Gln Pro Met Ile Ser Val Lys Cys Ser Pro<br>             280                      285                    290 | 920 |
| ttc cac ctg aag tca cgc tgt gtg ctg atg gga gat gca gct cat gcc<br>Phe His Leu Lys Ser Arg Cys Val Leu Met Gly Asp Ala Ala His Ala<br>             295                      300                    305 | 968 |
| atc gtc cca ttt ttt ggg caa gga atg aat gcg ggc ttt gaa gac tgc<br>Ile Val Pro Phe Phe Gly Gln Gly Met Asn Ala Gly Phe Glu Asp Cys<br>310                       315                    320 | 1016 |
| ttg gta ttt gat gag tta atg gac aaa ttc aat aat gat ctt agt gtg<br>Leu Val Phe Asp Glu Leu Met Asp Lys Phe Asn Asn Asp Leu Ser Val<br>325                       330                    335                340 | 1064 |
| tgc ctt cct gaa ttc tca aga ttt agg att cct gat gac cat gca att<br>Cys Leu Pro Glu Phe Ser Arg Phe Arg Ile Pro Asp Asp His Ala Ile | 1112 |

```
                    345                 350                 355
tca gac ctg tct atg tac aat tac ata gag atg cga gcg cat gtc aac      1160
Ser Asp Leu Ser Met Tyr Asn Tyr Ile Glu Met Arg Ala His Val Asn
            360                 365                 370 tct agg tgg ttc ctg ttt caa agg ctc ctg gat aaa ttt ctt cat gca      1208
Ser Arg Trp Phe Leu Phe Gln Arg Leu Leu Asp Lys Phe Leu His Ala
        375                 380                 385 cta atg cca tcc act ttc atc cct ctc tat acc atg gtc gcc ttc acc      1256
Leu Met Pro Ser Thr Phe Ile Pro Leu Tyr Thr Met Val Ala Phe Thr
    390                 395                 400 aga ata aga tac cac gag gca gtg ctg cgc tgg cat tgg caa aaa aag      1304
Arg Ile Arg Tyr His Glu Ala Val Leu Arg Trp His Trp Gln Lys Lys
405                 410                 415                 420 gtg ata aac aga gga ctc ttt gtc ctt ggg tcc ctg gta gcc att gga      1352
Val Ile Asn Arg Gly Leu Phe Val Leu Gly Ser Leu Val Ala Ile Gly
                425                 430                 435 agt gcc tac ata ctc gtg cac cac ctg tcc ccg aga cct ctg gaa ctc      1400
Ser Ala Tyr Ile Leu Val His His Leu Ser Pro Arg Pro Leu Glu Leu
            440                 445                 450 ctg aga tct gcc tgg acg gga acc tct ggc cac tgg aat agg agt gca      1448
Leu Arg Ser Ala Trp Thr Gly Thr Ser Gly His Trp Asn Arg Ser Ala
        455                 460                 465 gac att tct cca cga gtt cca tgg agt cac tag gacaaatgcc ccagttcact    1501
Asp Ile Ser Pro Arg Val Pro Trp Ser His
    470                 475 atccatagtg tcaacgttcc gggtagcaaa tgcttgattc ctcttcaata tcaagggaga   1561
aactcatgtt cccattgccg tcttcagttc actatgggaa aatcattgtc agcatataat   1621
taagttcgga gtggagggct gttttacag tgtctcatta ttttgcatgc ttggactggg   1681
ttcaattttt aaatttaaaa acacaataac caaaaaaaaa aaaaaaaaaa aa           1733

<210> SEQ ID NO 2
<211> LENGTH: 478
<212> TYPE: PRT
<213> ORGANISM: Rattus rattus

<400> SEQUENCE: 2

Met Ala Ser Ser Asp Thr Glu Gly Lys Arg Val Val Ile Gly Gly
  1               5                  10                  15

Gly Leu Val Gly Ala Leu Asn Ala Cys Phe Leu Ala Lys Arg Asn Phe
                 20                  25                  30

Gln Val Asp Val Tyr Glu Ala Arg Glu Asp Ile Arg Val Ala Asn Phe
             35                  40                  45

Met Arg Gly Arg Ser Ile Asn Leu Ala Leu Ser Tyr Arg Gly Arg Gln
         50                  55                  60

Ala Leu Lys Ala Val Gly Leu Glu Asp Gln Ile Val Ser Lys Gly Val
 65                  70                  75                  80

Pro Met Lys Ala Arg Met Ile His Ser Leu Ser Gly Lys Lys Ser Ala
                 85                  90                  95

Ile Pro Tyr Gly Asn Lys Ser Gln Tyr Ile Leu Ser Ile Ser Arg Glu
                100                 105                 110

Lys Leu Asn Lys Asp Leu Leu Thr Ala Val Glu Ser Tyr Pro Asn Ala
            115                 120                 125

Lys Val His Phe Gly His Lys Leu Ser Lys Cys Cys Pro Glu Glu Gly
        130                 135                 140

Ile Leu Thr Met Leu Gly Pro Asn Lys Val Pro Arg Asp Ile Thr Cys
145                 150                 155                 160
```

-continued

```
Asp Leu Ile Val Gly Cys Asp Gly Ala Tyr Ser Thr Val Arg Ala His
                165                 170                 175
Leu Met Lys Lys Pro Arg Phe Asp Tyr Ser Gln Gln Tyr Ile Pro His
            180                 185                 190
Gly Tyr Met Glu Leu Thr Ile Pro Pro Lys Asn Gly Glu Tyr Ala Met
        195                 200                 205
Glu Pro Asn Cys Leu His Ile Trp Pro Arg Asn Ala Phe Met Met Ile
    210                 215                 220
Ala Leu Pro Asn Met Asp Lys Ser Phe Thr Cys Thr Leu Phe Met Ser
225                 230                 235                 240
Phe Glu Glu Phe Glu Lys Leu Pro Thr His Ser Asp Val Leu Asp Phe
                245                 250                 255
Phe Gln Lys Asn Phe Pro Asp Ala Ile Pro Leu Met Gly Glu Gln Ala
            260                 265                 270
Leu Met Arg Asp Phe Phe Leu Leu Pro Ala Gln Pro Met Ile Ser Val
        275                 280                 285
Lys Cys Ser Pro Phe His Leu Lys Ser Arg Cys Val Leu Met Gly Asp
    290                 295                 300
Ala Ala His Ala Ile Val Pro Phe Phe Gly Gln Gly Met Asn Ala Gly
305                 310                 315                 320
Phe Glu Asp Cys Leu Val Phe Asp Glu Leu Met Asp Lys Phe Asn Asn
                325                 330                 335
Asp Leu Ser Val Cys Leu Pro Glu Phe Ser Arg Phe Arg Ile Pro Asp
            340                 345                 350
Asp His Ala Ile Ser Asp Leu Ser Met Tyr Asn Tyr Ile Glu Met Arg
        355                 360                 365
Ala His Val Asn Ser Arg Trp Phe Leu Phe Gln Arg Leu Leu Asp Lys
    370                 375                 380
Phe Leu His Ala Leu Met Pro Ser Thr Phe Ile Pro Leu Tyr Thr Met
385                 390                 395                 400
Val Ala Phe Thr Arg Ile Arg Tyr His Glu Ala Val Leu Arg Trp His
                405                 410                 415
Trp Gln Lys Lys Val Ile Asn Arg Gly Leu Phe Val Leu Gly Ser Leu
            420                 425                 430
Val Ala Ile Gly Ser Ala Tyr Ile Leu Val His His Leu Ser Pro Arg
        435                 440                 445
Pro Leu Glu Leu Leu Arg Ser Ala Trp Thr Gly Thr Ser Gly His Trp
    450                 455                 460
Asn Arg Ser Ala Asp Ile Ser Pro Arg Val Pro Trp Ser His
465                 470                 475

<210> SEQ ID NO 3
<211> LENGTH: 1628
<212> TYPE: DNA
<213> ORGANISM: Homo sapiens
<220> FEATURE:
<221> NAME/KEY: CDS
<222> LOCATION: (34)..(1494)

<400> SEQUENCE: 3
gcacagataa ttgtgaaaaa tacttcagca gtt atg gac tca tct gtc att caa    54
                                    Met Asp Ser Ser Val Ile Gln
                                      1               5 agg aaa aaa gta gct gtc att ggt ggt ggc ttg gtt ggc tca tta caa   102
Arg Lys Lys Val Ala Val Ile Gly Gly Gly Leu Val Gly Ser Leu Gln
         10                  15                  20
```

```
gca tgc ttt ctt gca aag agg aat ttc cag att gat gta tat gaa gct    150
Ala Cys Phe Leu Ala Lys Arg Asn Phe Gln Ile Asp Val Tyr Glu Ala
    25                  30                  35 agg gaa gat act cga gtg gct acc ttc aca cgt gga aga agc att aac    198
Arg Glu Asp Thr Arg Val Ala Thr Phe Thr Arg Gly Arg Ser Ile Asn
40                  45                  50                  55 tta gcc ctt tct cat aga gga cga caa gcc ttg aaa gct gtt ggc ctg    246
Leu Ala Leu Ser His Arg Gly Arg Gln Ala Leu Lys Ala Val Gly Leu
                60                  65                  70 gaa gat cag att gta tcc caa ggt att ccc atg aga gca aga atg atc    294
Glu Asp Gln Ile Val Ser Gln Gly Ile Pro Met Arg Ala Arg Met Ile
            75                  80                  85 cac tct ctt tca gga aaa aag tct gca att ccc tat ggg aca aag tct    342
His Ser Leu Ser Gly Lys Lys Ser Ala Ile Pro Tyr Gly Thr Lys Ser
        90                  95                  100 cag tat att ctt tct gta agc aga gaa aat cta aac aag gat cta ttg    390
Gln Tyr Ile Leu Ser Val Ser Arg Glu Asn Leu Asn Lys Asp Leu Leu
    105                 110                 115 act gct gct gag aaa tac ccc aat gtg aaa atg cac ttt aac cac agg    438
Thr Ala Ala Glu Lys Tyr Pro Asn Val Lys Met His Phe Asn His Arg
120                 125                 130                 135 ctg ttg aaa tgt aat cca gag gaa gga atg atc aca gtg ctt gga tct    486
Leu Leu Lys Cys Asn Pro Glu Glu Gly Met Ile Thr Val Leu Gly Ser
                140                 145                 150 gac aaa gtt ccc aaa gat gtc act tgt gac ctc att gta gga tgt gat    534
Asp Lys Val Pro Lys Asp Val Thr Cys Asp Leu Ile Val Gly Cys Asp
            155                 160                 165 gga gcc tat tca act gtc aga tct cac ctg atg aag aaa cct cgc ttt    582
Gly Ala Tyr Ser Thr Val Arg Ser His Leu Met Lys Lys Pro Arg Phe
        170                 175                 180 gat tac agt cag cag tac att cct cat ggg tac atg gag ttg act att    630
Asp Tyr Ser Gln Gln Tyr Ile Pro His Gly Tyr Met Glu Leu Thr Ile
    185                 190                 195 cca cct aag aac gga gat tat gcc atg gaa cct aat tat ctg cat att    678
Pro Pro Lys Asn Gly Asp Tyr Ala Met Glu Pro Asn Tyr Leu His Ile
200                 205                 210                 215 tgg cct aga aat acc ttt atg atg att gca ctt cct aac atg aac aaa    726
Trp Pro Arg Asn Thr Phe Met Met Ile Ala Leu Pro Asn Met Asn Lys
                220                 225                 230 tca ttc aca tgt act ttg ttc atg ccc ttt gaa gag ttt gaa aaa ctt    774
Ser Phe Thr Cys Thr Leu Phe Met Pro Phe Glu Glu Phe Glu Lys Leu
            235                 240                 245 cta acc agt aat gat gtg gta gat ttc ttc cag aaa tac ttt ccg gat    822
Leu Thr Ser Asn Asp Val Val Asp Phe Phe Gln Lys Tyr Phe Pro Asp
        250                 255                 260 gcc atc cct cta att gga gag aaa ctc cta gtg caa gat ttc ttc ctg    870
Ala Ile Pro Leu Ile Gly Glu Lys Leu Leu Val Gln Asp Phe Phe Leu
    265                 270                 275 ttg cct gcc cag ccc atg ata tct gta aag tgc tct tca ttt cac ttt    918
Leu Pro Ala Gln Pro Met Ile Ser Val Lys Cys Ser Ser Phe His Phe
280                 285                 290                 295 aaa tct cac tgt gta ctg ctg gga gat gca gct cat gct ata gtg ccg    966
Lys Ser His Cys Val Leu Leu Gly Asp Ala Ala His Ala Ile Val Pro
                300                 305                 310 ttt ttt ggg caa gga atg aat gcg ggc ttt gaa gac tgc ttg gta ttt   1014
Phe Phe Gly Gln Gly Met Asn Ala Gly Phe Glu Asp Cys Leu Val Phe
            315                 320                 325 gat gag tta atg gat aaa ttc agt aac gac ctt agt ttg tgt ctt cct   1062
Asp Glu Leu Met Asp Lys Phe Ser Asn Asp Leu Ser Leu Cys Leu Pro
```

-continued

```
         330              335              340
gtg ttc tca aga ttg aga atc cca gat gat cac gcg att tca gac cta   1110
Val Phe Ser Arg Leu Arg Ile Pro Asp Asp His Ala Ile Ser Asp Leu
    345              350              355 tcc atg tac aat tac ata gag atg cga gca cat gtc aac tca agc tgg   1158
Ser Met Tyr Asn Tyr Ile Glu Met Arg Ala His Val Asn Ser Ser Trp
360              365              370              375 ttc att ttt cag aag aac atg gag aga ttt ctt cat gcg att atg cca   1206
Phe Ile Phe Gln Lys Asn Met Glu Arg Phe Leu His Ala Ile Met Pro
            380              385              390 tcg acc ttt atc cct ctc tat aca atg gtc act ttt tcc aga ata aga   1254
Ser Thr Phe Ile Pro Leu Tyr Thr Met Val Thr Phe Ser Arg Ile Arg
        395              400              405 tac cat gag gct gtg cag cgt tgg cat tgg caa aaa aag gtg ata aac   1302
Tyr His Glu Ala Val Gln Arg Trp His Trp Gln Lys Lys Val Ile Asn
    410              415              420 aaa gga ctc ttt ttc ttg gga tca ctg ata gcc atc agc agt acc tac   1350
Lys Gly Leu Phe Phe Leu Gly Ser Leu Ile Ala Ile Ser Ser Thr Tyr
    425              430              435 cta ctt ata cac tac atg tca cca cga tct ttc ctc tgc ttg aga aga   1398
Leu Leu Ile His Tyr Met Ser Pro Arg Ser Phe Leu Cys Leu Arg Arg
440              445              450              455 cca tgg aac tgg ata gct cac ttc cgg aat aca aca tgt ttc ccc gca   1446
Pro Trp Asn Trp Ile Ala His Phe Arg Asn Thr Thr Cys Phe Pro Ala
            460              465              470 aag gcc gtg gac tcc cta gaa caa att tcc aat ctc att agc agg tga   1494
Lys Ala Val Asp Ser Leu Glu Gln Ile Ser Asn Leu Ile Ser Arg
        475              480              485 tagaaaggtt ttgtggtagc aaatgcatga tttctctgtg accaaaatta agcatgaaaa   1554
aaatgtttcc attgccatat tgattcact agtggaagat agtgttctgc ttataattaa   1614
actgaatgta gagt                                                    1628

<210> SEQ ID NO 4
<211> LENGTH: 486
<212> TYPE: PRT
<213> ORGANISM: Homo sapiens

<400> SEQUENCE: 4

Met Asp Ser Ser Val Ile Gln Arg Lys Lys Val Ala Val Ile Gly Gly
1               5                   10                  15

Gly Leu Val Gly Ser Leu Gln Ala Cys Phe Leu Ala Lys Arg Asn Phe
            20                  25                  30

Gln Ile Asp Val Tyr Glu Ala Arg Glu Asp Thr Arg Val Ala Thr Phe
        35                  40                  45

Thr Arg Gly Arg Ser Ile Asn Leu Ala Leu Ser His Arg Gly Arg Gln
    50                  55                  60

Ala Leu Lys Ala Val Gly Leu Glu Asp Gln Ile Val Ser Gln Gly Ile
65                  70                  75                  80

Pro Met Arg Ala Arg Met Ile His Ser Leu Ser Gly Lys Lys Ser Ala
                85                  90                  95

Ile Pro Tyr Gly Thr Lys Ser Gln Tyr Ile Leu Ser Val Ser Arg Glu
            100                 105                 110

Asn Leu Asn Lys Asp Leu Leu Thr Ala Ala Glu Lys Tyr Pro Asn Val
        115                 120                 125

Lys Met His Phe Asn His Arg Leu Leu Lys Cys Asn Pro Glu Glu Gly
    130                 135                 140
```

```
Met Ile Thr Val Leu Gly Ser Asp Lys Val Pro Lys Asp Val Thr Cys
145                 150                 155                 160

Asp Leu Ile Val Gly Cys Asp Gly Ala Tyr Ser Thr Val Arg Ser His
            165                 170                 175

Leu Met Lys Lys Pro Arg Phe Asp Tyr Ser Gln Gln Tyr Ile Pro His
        180                 185                 190

Gly Tyr Met Glu Leu Thr Ile Pro Pro Lys Asn Gly Asp Tyr Ala Met
    195                 200                 205

Glu Pro Asn Tyr Leu His Ile Trp Pro Arg Asn Thr Phe Met Met Ile
210                 215                 220

Ala Leu Pro Asn Met Asn Lys Ser Phe Thr Cys Thr Leu Phe Met Pro
225                 230                 235                 240

Phe Glu Glu Phe Glu Lys Leu Leu Thr Ser Asn Asp Val Val Asp Phe
                245                 250                 255

Phe Gln Lys Tyr Phe Pro Asp Ala Ile Pro Leu Ile Gly Glu Lys Leu
            260                 265                 270

Leu Val Gln Asp Phe Phe Leu Leu Pro Ala Gln Pro Met Ile Ser Val
        275                 280                 285

Lys Cys Ser Ser Phe His Phe Lys Ser His Cys Val Leu Leu Gly Asp
290                 295                 300

Ala Ala His Ala Ile Val Pro Phe Phe Gly Gln Gly Met Asn Ala Gly
305                 310                 315                 320

Phe Glu Asp Cys Leu Val Phe Asp Glu Leu Met Asp Lys Phe Ser Asn
                325                 330                 335

Asp Leu Ser Leu Cys Leu Pro Val Phe Ser Arg Leu Arg Ile Pro Asp
            340                 345                 350

Asp His Ala Ile Ser Asp Leu Ser Met Tyr Asn Tyr Ile Glu Met Arg
        355                 360                 365

Ala His Val Asn Ser Ser Trp Phe Ile Phe Gln Lys Asn Met Glu Arg
    370                 375                 380

Phe Leu His Ala Ile Met Pro Ser Thr Phe Ile Pro Leu Tyr Thr Met
385                 390                 395                 400

Val Thr Phe Ser Arg Ile Arg Tyr His Glu Ala Val Gln Arg Trp His
                405                 410                 415

Trp Gln Lys Lys Val Ile Asn Lys Gly Leu Phe Phe Leu Gly Ser Leu
            420                 425                 430

Ile Ala Ile Ser Ser Thr Tyr Leu Leu Ile His Tyr Met Ser Pro Arg
        435                 440                 445

Ser Phe Leu Cys Leu Arg Arg Pro Trp Asn Trp Ile Ala His Phe Arg
450                 455                 460

Asn Thr Thr Cys Phe Pro Ala Lys Ala Val Asp Ser Leu Glu Gln Ile
465                 470                 475                 480

Ser Asn Leu Ile Ser Arg
                485

<210> SEQ ID NO 5
<211> LENGTH: 5000
<212> TYPE: DNA
<213> ORGANISM: Homo sapiens
<220> FEATURE:
<221> NAME/KEY: CDS
<222> LOCATION: (47)..(1507)

<400> SEQUENCE: 5
ggcacgagca gaagcaacaa taattgtgaa aaatacttca gcagtt atg gac tca      55
                                                 Met Asp Ser
```

-continued

1

| | | | | | | | | | | | | | | | | |
|---|---|---|---|---|---|---|---|---|---|---|---|---|---|---|---|---|
| tct | gtc | att | caa | agg | aaa | aaa | gta | gct | gtc | att | ggt | ggt | ggc | ttg | gtt | 103 |
| Ser | Val | Ile | Gln | Arg | Lys | Lys | Val | Ala | Val | Ile | Gly | Gly | Gly | Leu | Val | |
| | 5 | | | | 10 | | | | | 15 | | | | | | |

| ggc | tca | tta | caa | gca | tgc | ttt | ctt | gca | aag | agg | aat | ttc | cag | att | gat | 151 |
| Gly | Ser | Leu | Gln | Ala | Cys | Phe | Leu | Ala | Lys | Arg | Asn | Phe | Gln | Ile | Asp | |
| 20 | | | | 25 | | | | | 30 | | | | | | 35 | |

| gta | tat | gaa | gct | agg | gaa | gat | act | cga | gtg | gct | acc | ttc | aca | cgt | gga | 199 |
| Val | Tyr | Glu | Ala | Arg | Glu | Asp | Thr | Arg | Val | Ala | Thr | Phe | Thr | Arg | Gly | |
| | | | 40 | | | | | 45 | | | | | 50 | | | |

| aga | agc | att | aac | tta | gcc | ctt | tct | cat | aga | gga | cga | caa | gcc | ttg | aaa | 247 |
| Arg | Ser | Ile | Asn | Leu | Ala | Leu | Ser | His | Arg | Gly | Arg | Gln | Ala | Leu | Lys | |
| | | | 55 | | | | | 60 | | | | | 65 | | | |

| gct | gtt | ggc | ctg | gaa | gat | cag | att | gta | tcc | caa | ggt | att | ccc | atg | aga | 295 |
| Ala | Val | Gly | Leu | Glu | Asp | Gln | Ile | Val | Ser | Gln | Gly | Ile | Pro | Met | Arg | |
| | | 70 | | | | | 75 | | | | | 80 | | | | |

| gca | aga | atg | atc | cac | tct | ctt | tca | gga | aaa | aag | tct | gca | att | ccc | tat | 343 |
| Ala | Arg | Met | Ile | His | Ser | Leu | Ser | Gly | Lys | Lys | Ser | Ala | Ile | Pro | Tyr | |
| | 85 | | | | | 90 | | | | | 95 | | | | | |

| ggg | aca | aag | tct | cag | tat | att | ctt | tct | gta | agc | aga | gaa | aat | cta | aac | 391 |
| Gly | Thr | Lys | Ser | Gln | Tyr | Ile | Leu | Ser | Val | Ser | Arg | Glu | Asn | Leu | Asn | |
| 100 | | | | | 105 | | | | | 110 | | | | | 115 | |

| aag | gat | cta | ttg | act | gct | gct | gag | aaa | tac | ccc | aat | gtg | aaa | atg | cac | 439 |
| Lys | Asp | Leu | Leu | Thr | Ala | Ala | Glu | Lys | Tyr | Pro | Asn | Val | Lys | Met | His | |
| | | | | 120 | | | | | 125 | | | | | 130 | | |

| ttt | aac | cac | agg | ctg | ttg | aaa | tgt | aat | cca | gag | gaa | gga | atg | atc | aca | 487 |
| Phe | Asn | His | Arg | Leu | Leu | Lys | Cys | Asn | Pro | Glu | Glu | Gly | Met | Ile | Thr | |
| | | 135 | | | | | 140 | | | | | 145 | | | | |

| gtg | ctt | gga | tct | gac | aaa | gtt | ccc | aaa | gat | gtc | act | tgt | gac | ctc | att | 535 |
| Val | Leu | Gly | Ser | Asp | Lys | Val | Pro | Lys | Asp | Val | Thr | Cys | Asp | Leu | Ile | |
| | 150 | | | | | 155 | | | | | 160 | | | | | |

| gta | gga | tgt | gat | gga | gcc | tat | tca | act | gtc | aga | tct | cac | ctg | atg | aag | 583 |
| Val | Gly | Cys | Asp | Gly | Ala | Tyr | Ser | Thr | Val | Arg | Ser | His | Leu | Met | Lys | |
| | 165 | | | | | 170 | | | | | 175 | | | | | |

| aaa | cct | cgc | ttt | gat | tac | agt | cag | cag | tac | att | cct | cat | ggg | tac | atg | 631 |
| Lys | Pro | Arg | Phe | Asp | Tyr | Ser | Gln | Gln | Tyr | Ile | Pro | His | Gly | Tyr | Met | |
| 180 | | | | | 185 | | | | | 190 | | | | | 195 | |

| gag | ttg | act | att | cca | cct | aag | aac | gga | gat | tat | gcc | atg | gaa | cct | aat | 679 |
| Glu | Leu | Thr | Ile | Pro | Pro | Lys | Asn | Gly | Asp | Tyr | Ala | Met | Glu | Pro | Asn | |
| | | | | 200 | | | | | 205 | | | | | 210 | | |

| tat | ctg | cat | att | tgg | cct | aga | aat | acc | ttt | atg | atg | att | gca | ctt | cct | 727 |
| Tyr | Leu | His | Ile | Trp | Pro | Arg | Asn | Thr | Phe | Met | Met | Ile | Ala | Leu | Pro | |
| | | | 215 | | | | | 220 | | | | | 225 | | | |

| aac | atg | aac | aaa | tca | ttc | aca | tgt | act | ttg | ttc | atg | ccc | ttt | gaa | gag | 775 |
| Asn | Met | Asn | Lys | Ser | Phe | Thr | Cys | Thr | Leu | Phe | Met | Pro | Phe | Glu | Glu | |
| | | 230 | | | | | 235 | | | | | 240 | | | | |

| ttt | gaa | aaa | ctt | cta | acc | agt | aat | gat | gtg | gta | gat | ttc | ttc | cag | aaa | 823 |
| Phe | Glu | Lys | Leu | Leu | Thr | Ser | Asn | Asp | Val | Val | Asp | Phe | Phe | Gln | Lys | |
| | 245 | | | | | 250 | | | | | 255 | | | | | |

| tac | ttt | ccg | gat | gcc | atc | cct | cta | att | gga | gag | aaa | ctc | cta | gtg | caa | 871 |
| Tyr | Phe | Pro | Asp | Ala | Ile | Pro | Leu | Ile | Gly | Glu | Lys | Leu | Leu | Val | Gln | |
| 260 | | | | 265 | | | | | 270 | | | | | 275 | | |

| gat | ttc | ttc | ctg | ttg | cct | gcc | cag | ccc | atg | ata | tct | gta | aag | tgc | tct | 919 |
| Asp | Phe | Phe | Leu | Leu | Pro | Ala | Gln | Pro | Met | Ile | Ser | Val | Lys | Cys | Ser | |
| | | | 280 | | | | | 285 | | | | | 290 | | | |

| tca | ttt | cac | ttt | aaa | tct | cac | tgt | gta | ctg | ctg | gga | gat | gca | gct | cat | 967 |
| Ser | Phe | His | Phe | Lys | Ser | His | Cys | Val | Leu | Leu | Gly | Asp | Ala | Ala | His | |
| | | 295 | | | | | 300 | | | | | 305 | | | | |

| gct | ata | gtg | ccg | ttt | ttt | ggg | caa | gga | atg | aat | gcg | ggc | ttt | gaa | gac | 1015 |

-continued

```
Ala Ile Val Pro Phe Phe Gly Gln Gly Met Asn Ala Gly Phe Glu Asp
        310                 315                 320 tgc ttg gta ttt gat gag tta atg gat aaa ttc agt aac gac ctt agt      1063
Cys Leu Val Phe Asp Glu Leu Met Asp Lys Phe Ser Asn Asp Leu Ser
325                 330                 335 ttg tgt ctt cct gtg ttc tca aga ttg aga atc cca gat gat cac gcg      1111
Leu Cys Leu Pro Val Phe Ser Arg Leu Arg Ile Pro Asp Asp His Ala
340                 345                 350                 355 att tca gac cta tcc atg tac aat tac ata gag atg cga gca cat gtc      1159
Ile Ser Asp Leu Ser Met Tyr Asn Tyr Ile Glu Met Arg Ala His Val
                360                 365                 370 aac tca agc tgg ttc att ttt cag aag aac atg gag aga ttt ctt cat      1207
Asn Ser Ser Trp Phe Ile Phe Gln Lys Asn Met Glu Arg Phe Leu His
            375                 380                 385 gcg att atg cca tcg acc ttt atc cct ctc tat aca atg gtc act ttt      1255
Ala Ile Met Pro Ser Thr Phe Ile Pro Leu Tyr Thr Met Val Thr Phe
        390                 395                 400 tcc aga ata aga tac cat gag gct gtg cag cgt tgg cat tgg caa aaa      1303
Ser Arg Ile Arg Tyr His Glu Ala Val Gln Arg Trp His Trp Gln Lys
    405                 410                 415 aag gtg ata aac aaa gga ctc ttt ttc ttg gga tca ctg ata gcc atc      1351
Lys Val Ile Asn Lys Gly Leu Phe Phe Leu Gly Ser Leu Ile Ala Ile
420                 425                 430                 435 agc agt acc tac cta ctt ata cac tac atg tca cca cga tct ttc ctc      1399
Ser Ser Thr Tyr Leu Leu Ile His Tyr Met Ser Pro Arg Ser Phe Leu
                440                 445                 450 tgc ttg aga aga cca tgg aac tgg ata gct cac ttc cgg aat aca aca      1447
Cys Leu Arg Arg Pro Trp Asn Trp Ile Ala His Phe Arg Asn Thr Thr
            455                 460                 465 tgt ttc ccc gca aag gcc gtg gac tcc cta gaa caa att tcc aat ctc      1495
Cys Phe Pro Ala Lys Ala Val Asp Ser Leu Glu Gln Ile Ser Asn Leu
        470                 475                 480 att agc agg tga tagaaaggtt tgtggtagc aaatgcatga tttctctgtg           1547
Ile Ser Arg
    485 accaaaatta agcatgaaaa aaatgttttcc attgccatat ttgattcact agtggaagat   1607 agtgttctgc ttataattaa actgaatgta gagtatctct gtatgttaat tgcaattact   1667 ggttgggggg tgcattttaa aagatgaaac atgcagcttc cctacattac acacactcag   1727 gttgagtcat tctaactata aaagtgcaat gactaagatc cttcacttct ctgaaagtaa   1787 ggccctagat gcctcaggga agacagtaat catgcctttt ctttaaaaga cacaatagga   1847 ctcgcaacag cattgactca acacctagga ctaaaaatca caacttaact agcatgttaa   1907 ctgcactttt cattacgtga atggaactta cctaaccaca gggctcagac ttactagata   1967 aaaccagaaa tggaaataag gaattcaggg gagttccaga gacttacaaa atgaactcat   2027 tttattttcc caccttcaaa tataagtatt atcatctatc tgtttatcgt ctatctatct   2087 atcatctatc tatctatcta tcatctatct atctatctat ctatctatct atctatctat   2147 ctatctatct atctctattt atttatgtat ttagagatca ggtctcactc tgttgaccag   2207 gctggagtgc agtggtgaga tctgggttca ctgcaacctc tgcctcctgg gctcaagcaa   2267 tcctcccact tcagcctccc aaatagctgg ggctaccatg gtattttca gtagagaccg   2327 ggtcttgcca tgctgcccag gccagtctca aactcctggc tcatgtgat ctgcccacct   2387 cagcctccca agtacaggg attagagttg tgagccaccg ctgccagccc agagttaccc   2447 tctaaagata agaaaaaggc tattaatatc atactaagtg aaggacagga aagggtttta   2507
```

```
ttcataaatt aaatgtctac atgtgccaga atggaaagga aacaagggga gacaactttt 2567 atagaaatac aaagccatta ctttattcaa tttcagaccc tcagaagcaa tttactaatt 2627 tattcttcga ctacatactg cagcagaacc agcaatacac ttgattttta aaagcacatt 2687 tagtgaaatg ttttctttgg ttcatccttc tttaacaggc tgctgagtca ctcagaaatc 2747 cttcaaacat gattaattat gaagatgaaa cactagagtc atataagaaa taaaaattgg 2807 gcaataaaat aaaatgattc agtgtttctt ttctatattg tcaatgaaaa ccttgagttc 2867 taataatcca tgttcagttt gtagggaaag aaaaaataat ttttccttct acccacttta 2927 ggttccttgg ctggggcccc tataacaaaa gacagattga caagagaaaa acaaacataa 2987 atttattagc gggtatatgt aatatatatg tgggaaatac aggggaatga gcaaatctca 3047 aagagctggc gtcttagaac tccctggctt atatagcatc gacaaagaac agtaaatttt 3107 tagagaaaca acaaaacaaa gaaaaagagc tttgagtctg taggggcagc aatttggggg 3167 aagcaaatat atgggagttt gccttgtaga ttcctctggt ggtggtctcc aggctgacaa 3227 ggattcaaag ttgtctctga aactcctctt tgtcatactg cacatataaa acgtcttttg 3287 tttccaacaa gaggatttct ttttcattct agaattatct ccttgataac ttgatcagat 3347 ataggacatg acactgaata gagtccaaca gtacaaaaaa aattcagtat gttctagcta 3407 cttcacacat gtgtacgcga cagttatttt tacagtaagg tattttcgag aaaaatgcat 3467 tacgtgtttt ggaaaataga gtaatttaaa aaatatattt gaaatgaaaa ctccaacac 3527 attagaagat gatgatgtta gatgcccatc gtgtgccaca agtggttttt tcattatgta 3587 aagcacccgt tgaattaaaa gaatttgttt ttgttcaacc tcttcctgag gcccaagagc 3647 atatgggcaa ttcggatttc ctgctggacc acaaggttct gttgatatta catagaaacg 3707 ggtattccag acacttctta tgatgaaagt ccaaaagtgg catccaattt aaggccccat 3767 cttcgttgc cattcttcat tcctacaaag gacgaacttg gattacatca actttggacc 3827 cattggtttt gtcgctgtcg tcaactgaca gtgattcacc actggtgatg ataaaaatga 3887 tggaagaaga gttgaaagtc acttttttct ttggcctgtc cccatctttc tgtgacatca 3947 caatgggtct gatctgcatt tcacttccag ctgctggtag gtctttagca ggcctctggc 4007 acctcagcag tcggaggcac agaagctgca aaagggatct tcgaaactgg gcagagaaaa 4067 aataaagtgg aatattaagt aaaagttggg cactaatctg gattaacatt cgaggaaatc 4127 agttgagctg atttaagttg ttttttgttt gttagcaggt gtggatgtgg ggttatgtgg 4187 tcatgctcag atctacctaa atcaccccag agctttatgt ctttttattca ttctaaatct 4247 tattaaccgg aatatgtagg accatttcaa taccttgtaa tcctccaagc ttcaatctgc 4307 acacactttc tatgagggca ggtacaacta ttaagagatt ttgaacatta agttagtcca 4367 caaatattca gtgggcatct actaggtgac agccactgtg ctataattag agacttttta 4427 ctataagcat caaaaacaga taaggctctt cctggcagag tttacagcct ggtgtacttg 4487 ctaatgtctc tttaattagg tgaagaattt ttttttttcta tcgaaattac taatcagttg 4547 gggaaaaaaa tactatagca gacagcacta atgtcatcaa caaacattgt tcttctccgt 4607 gtcctgggta caacatcgaa taatatttct tggcctcctt tccgcttctc ctctctgctg 4667 ttcctctcta caagaacctg ggaggccaac gcctaaagat cataatatca caatggaagg 4727 aacctagatt cctaaatgac tgcataggac agatcccatc tcctccaccc aatacattat 4787 tagactgaac tgtgacctga aatgagcaat aaactctgta ttaattcact gaaatgttgg 4847 ggttgcttgt tatagtagtc ggtccatcat gaccagtaaa acataaatca aaagttaatg 4907
```

```
taattgttat cccattattt agagcgaaat aaatgttgaa tatatggact ttctcagatt  4967
aggaaatacc aattaaaaat ataataaata gct                               5000
```

<210> SEQ ID NO 6
<211> LENGTH: 486
<212> TYPE: PRT
<213> ORGANISM: Homo sapiens

<400> SEQUENCE: 6

```
Met Asp Ser Ser Val Ile Gln Arg Lys Lys Val Ala Val Ile Gly Gly
 1               5                  10                  15

Gly Leu Val Gly Ser Leu Gln Ala Cys Phe Leu Ala Lys Arg Asn Phe
                20                  25                  30

Gln Ile Asp Val Tyr Glu Ala Arg Glu Asp Thr Arg Val Ala Thr Phe
            35                  40                  45

Thr Arg Gly Arg Ser Ile Asn Leu Ala Leu Ser His Arg Gly Arg Gln
        50                  55                  60

Ala Leu Lys Ala Val Gly Leu Glu Asp Gln Ile Val Ser Gln Gly Ile
    65                  70                  75                  80

Pro Met Arg Ala Arg Met Ile His Ser Leu Ser Gly Lys Lys Ser Ala
                85                  90                  95

Ile Pro Tyr Gly Thr Lys Ser Gln Tyr Ile Leu Ser Val Ser Arg Glu
            100                 105                 110

Asn Leu Asn Lys Asp Leu Leu Thr Ala Ala Glu Lys Tyr Pro Asn Val
        115                 120                 125

Lys Met His Phe Asn His Arg Leu Leu Lys Cys Asn Pro Glu Glu Gly
    130                 135                 140

Met Ile Thr Val Leu Gly Ser Asp Lys Val Pro Lys Asp Val Thr Cys
145                 150                 155                 160

Asp Leu Ile Val Gly Cys Asp Gly Ala Tyr Ser Thr Val Arg Ser His
                165                 170                 175

Leu Met Lys Lys Pro Arg Phe Asp Tyr Ser Gln Gln Tyr Ile Pro His
            180                 185                 190

Gly Tyr Met Glu Leu Thr Ile Pro Pro Lys Asn Gly Asp Tyr Ala Met
        195                 200                 205

Glu Pro Asn Tyr Leu His Ile Trp Pro Arg Asn Thr Phe Met Met Ile
    210                 215                 220

Ala Leu Pro Asn Met Asn Lys Ser Phe Thr Cys Thr Leu Phe Met Pro
225                 230                 235                 240

Phe Glu Glu Phe Glu Lys Leu Leu Thr Ser Asn Asp Val Val Asp Phe
                245                 250                 255

Phe Gln Lys Tyr Phe Pro Asp Ala Ile Pro Leu Ile Gly Glu Lys Leu
            260                 265                 270

Leu Val Gln Asp Phe Phe Leu Leu Pro Ala Gln Pro Met Ile Ser Val
        275                 280                 285

Lys Cys Ser Ser Phe His Phe Lys Ser His Cys Val Leu Leu Gly Asp
    290                 295                 300

Ala Ala His Ala Ile Val Pro Phe Phe Gly Gln Gly Met Asn Ala Gly
305                 310                 315                 320

Phe Glu Asp Cys Leu Val Phe Asp Glu Leu Met Asp Lys Phe Ser Asn
                325                 330                 335

Asp Leu Ser Leu Cys Leu Pro Val Phe Ser Arg Leu Arg Ile Pro Asp
            340                 345                 350
```

-continued

```
Asp His Ala Ile Ser Asp Leu Ser Met Tyr Asn Tyr Ile Glu Met Arg
            355                 360                 365

Ala His Val Asn Ser Ser Trp Phe Ile Phe Gln Lys Asn Met Glu Arg
        370                 375                 380

Phe Leu His Ala Ile Met Pro Ser Thr Phe Ile Pro Leu Tyr Thr Met
385                 390                 395                 400

Val Thr Phe Ser Arg Ile Arg Tyr His Glu Ala Val Gln Arg Trp His
                405                 410                 415

Trp Gln Lys Lys Val Ile Asn Lys Gly Leu Phe Phe Leu Gly Ser Leu
            420                 425                 430

Ile Ala Ile Ser Ser Thr Tyr Leu Leu Ile His Tyr Met Ser Pro Arg
        435                 440                 445

Ser Phe Leu Cys Leu Arg Arg Pro Trp Asn Trp Ile Ala His Phe Arg
    450                 455                 460

Asn Thr Thr Cys Phe Pro Ala Lys Ala Val Asp Ser Leu Glu Gln Ile
465                 470                 475                 480

Ser Asn Leu Ile Ser Arg
            485
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 7
caggaattcc atatggactc atctgtc                                          27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 8
cgggatcccg ctatcacctg ctaatga                                          27

<210> SEQ ID NO 9
<211> LENGTH: 460
<212> TYPE: PRT
<213> ORGANISM: Saccharomyces cerevisiae

<400> SEQUENCE: 9

```
Met Ser Glu Ser Val Ala Ile Ile Gly Ala Gly Leu Val Gly Cys Leu
1               5                   10                  15

Ala Ala Leu Ala Phe Ser Lys Glu Gly Tyr Asn Val Thr Leu Tyr Asp
            20                  25                  30

Phe Arg Gln Asp His Arg Leu Asp Thr Thr Lys Asn Lys Asn Leu Lys
        35                  40                  45

Ser Ile Asn Leu Ala Ile Ser Ala Arg Gly Ile Asp Ala Leu Lys Ser
    50                  55                  60

Ile Asp Pro Asp Ala Cys Glu His Ile Leu Gln Asp Met Ile Pro Met
65                  70                  75                  80

Lys Gly Arg Met Ile His Ser Leu Lys Gly Arg Gln Glu Ser Gln Leu
            85                  90                  95
```

```
                                        -continued

Tyr Gly Leu His Gly Glu Ala Ile Asn Ser Ile Asn Arg Ser Val Leu
            100                 105                 110

Asn Asn Ser Leu Leu Asp Glu Leu Glu Lys Ser Thr Thr Glu Leu Lys
            115                 120                 125

Phe Gly His Lys Leu Val Lys Ile Glu Trp Thr Asp Asp Lys Gln Ile
            130                 135                 140

Cys His Phe Ala Ile Gly Glu Asp Leu Lys Thr Pro His Thr Glu Lys
145                 150                 155                 160

Tyr Asp Phe Val Ile Gly Cys Asp Gly Ala Tyr Ser Ala Thr Arg Ser
                165                 170                 175

Gln Met Gln Arg Lys Val Glu Met Asp Phe Ser Gln Glu Tyr Met Asn
            180                 185                 190

Leu Arg Tyr Ile Glu Leu Tyr Ile Pro Pro Thr Glu Glu Phe Lys Pro
            195                 200                 205

Asn Tyr Gly Gly Asn Phe Ala Ile Ala Pro Asp His Leu His Ile Trp
            210                 215                 220

Pro Arg His Lys Phe Met Leu Ile Ala Leu Ala Asn Ser Asp Gly Ser
225                 230                 235                 240

Phe Thr Ser Thr Phe Phe Gly Ser Lys Asp Gln Ile Ser Leu Leu Thr
                245                 250                 255

Thr Ser Lys Ser Arg Val Arg Glu Phe Leu Ile Glu Asn Phe Pro Asp
            260                 265                 270

Ile Ile Asn Ile Met Asp Leu Asp Asp Ala Val Lys Phe Arg Ile Thr
            275                 280                 285

Tyr Pro Lys Glu Ser Leu Val Cys Val Asn Cys Lys Pro Tyr Asp Val
            290                 295                 300

Pro Gly Gly Lys Ala Ile Leu Leu Gly Asp Ala Ala His Ala Met Val
305                 310                 315                 320

Pro Phe Tyr Gly Gln Gly Met Asn Cys Gly Phe Glu Asp Val Arg Ile
                325                 330                 335

Leu Met Ala Leu Leu Lys Lys His Ser Gly Asp Arg Ser Arg Ala Phe
            340                 345                 350

Thr Glu Tyr Thr Gln Thr Arg His Lys Asp Leu Val Ser Ile Thr Glu
            355                 360                 365

Leu Ala Lys Arg Asn Tyr Lys Glu Met Ser His Asp Val Ile Ser Lys
            370                 375                 380

Arg Phe Leu Leu Arg Lys Lys Leu Asp Ala Leu Phe Ser Ile Ile Met
385                 390                 395                 400

Lys Asp Lys Trp Ile Pro Leu Tyr Thr Met Ile Ser Phe Arg Ser Asp
                405                 410                 415

Ile Ser Tyr Ser Arg Ala Leu Glu Arg Ala Gly Lys Gln Thr Arg Ile
            420                 425                 430

Leu Lys His Leu Glu Ser Leu Thr Leu Gly Met Leu Ser Ile Gly Gly
            435                 440                 445

Tyr Lys Leu Phe Lys Glu Leu Thr Arg Glu Arg Ser
450                 455                 460
```

RECOMBINANT KYNURENINE-3-HYDROXYLASE ENZYME AND PROCESS FOR ITS PREPARATION

BACKGROUND OF THE INVENTION

The present invention concerns DNA sequences encoding for kynurenine-3-hydroxylase (kyn-3-OHase).

This enzyme is a flavin-containing monooxygenase which is localized in the outer mitochondrial membrane (Okamoto H., Yamamoto S., Nozaki M. and Hayaishi O. 1967. Biochem. Biophys. Res. Commun. 26: 309–314); it catalyses the 3 hydroxylation of L-kynurenine (L-kyn), an intermediate in the oxidative metabolism of tryptophan (DeCastro F. T., Price J. M. and Brown R. R., 1956. J. Am. Chem. Soc. 78: 2900–2904).

The kynurenine pathway (see the scheme below) is the major route of peripheral tryptophan metabolism in mammals: most of this metabolism takes place in the liver. The abbreviations used are the following: IDO, Indoleamine 2,3-dioxygenase; TDO, Tryptophan 2,3-dioxygenase; ED, 3-hydroxyanthranilate 3,4-dioxygenase; QPRT, Quinolinate phosphoribosyltransferase; ATP, Adenosine 5'-triphosphate; NAD, Nicotinamide adenine dinucleotide; NMN, Nicotinamide mononucleotide.

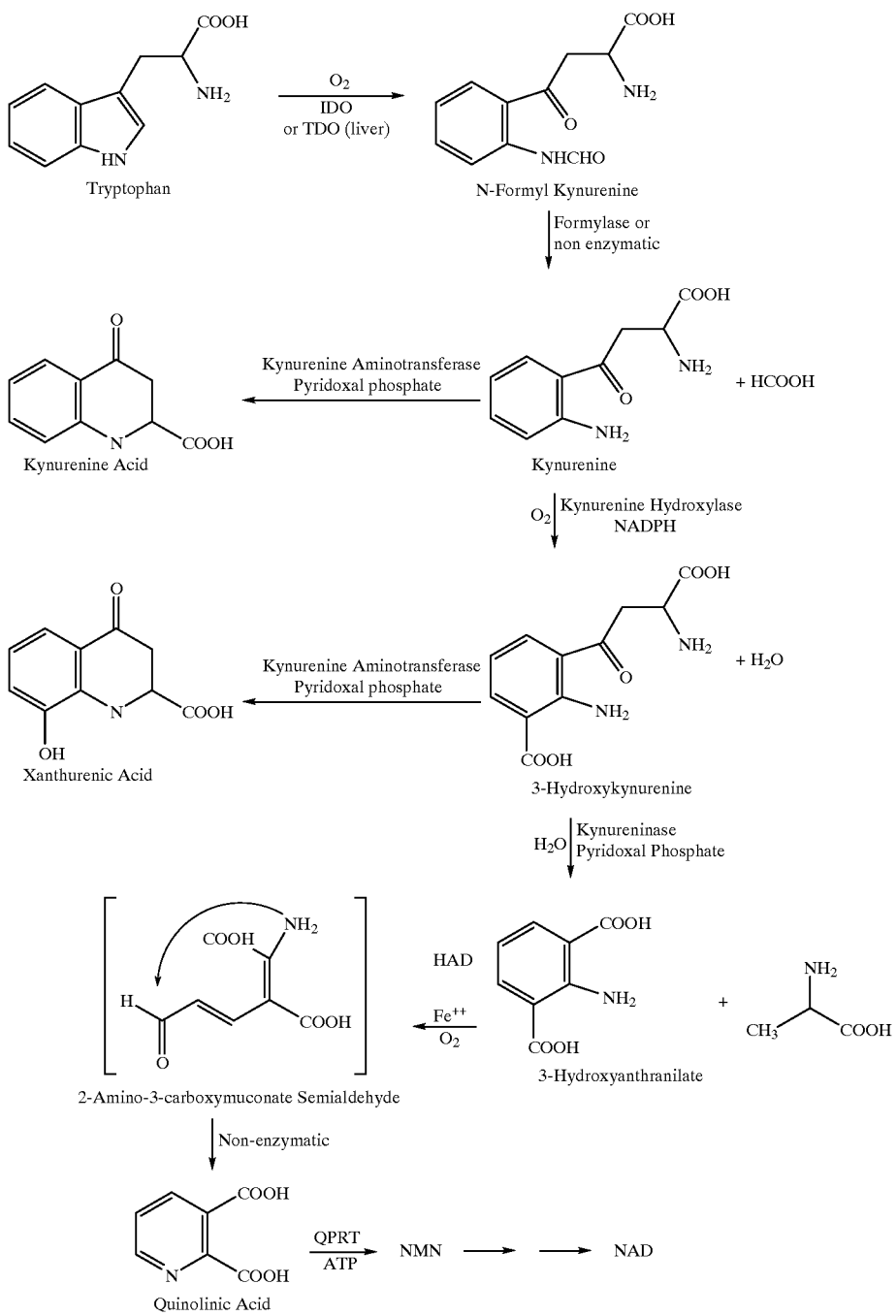

This pathway not only provides a route for total oxidation of tryptophan to acetyl-Co-A, but it is also responsible for the synthesis de novo of the nicotinamide nucleotide coenzymes NAD and NADP (Bender D. A. and McCreanor G. M. 1985. Biochem. Soc. Trans. 13:441–443).

Most of the current interest in this pathway arises from the observations that two intermediate metabolites, kynurenic acid (KYNA) and quinolinic acid (QUIN), seem to play a significant role in neurological diseases, the first acting as a neuroprotectant and the second as a neurotoxic agent. Kyn-3-OHase is the first enzyme in the route of production of QUIN.

The importance of QUIN as a neurotoxic agent was first evident from work by Lapin (1978. J. Neural. Trans. 42:37–43) who demonstrated that the administration of QUIN to rats caused convulsions. This was not sufficient to classify QUIN as a neurotoxin; its action in the central nervous system was better clarified when electrophysiological studies revealed that it was an agonist at the excitatory amino acid receptor sites normally activated by glutamate and aspartate (Stone T. W. and Perkins M. N., 1981. Eur J. Pharmacol. 72: 411–412).

Moreover, using the intrastriatal injection model, QUIN toxicity has been shown to be mediated through the N-methyl-D-aspartate (NMDA) receptors (Beal M., Kowall N., Swartz K. J., Ferrante R. J. and Martin J. B. 1989. J. Neurosci. 8: 3901–3908; Foster A. C., Gill R. and Woodruff G. N. 1988. J. Neurosci. 8: 4745–4754). Consistent with the involvment of NMDA receptors were the studies that showed reversal of QUIN-induced damage pathology by competitive NMDA antagonists (Foster A. C., Vezzani A., French E. D. and Schwarcz R. 1984. Neurosci. Lett. 48: 273–278; Leeson P. D., Baker R., Carling R. W., Curtis N. R., Moore K. W., Williams B. J. et al. 1991. J. Med. Chem. 34: 1243–1252).

It is becoming clear that some of the most important functions of the nervous system, such as synaptic plasticity and synapse formation, critically depend on the behavior of NMDA receptor channels and that neurological damages caused by a variety of pathological states can result from exaggerated activation of NMDA receptor channels (For a review see: Mori H. and Mishina M. 1995. Neuropharmacology 34: 1219–1237). Excessive activation of these receptors may play an important role in the neuronal injury associated with several disease states, including hypoxia-ischemia (Simon R. P., Swan J. H., Griffiths T. and Meldrum B. A. 1984. Science 226: 850–852), hypoglycemia (Wieloch T. 1985. Science 230: 681–683) and Huntington's disease (Schwarcz R., Whetsell W. O. Jr. and Mangano R. M. 1983. Science 219: 316–318. Koh J. Y., Peters S. and Choi D. W. 1986. Science 234: 73–76).

Assuming that QUIN is pathogenic for certain disorders, it is desirable to inhibit its formation. To accomplish this goal, knowledge must be gained about the enzymes that make QUIN and the sites at which the pathway is controlled.

In theory, QUIN could be formed in the brain in several ways (see the Kynurenine pathway above): from tryptophan, as in macrophages and in liver, or from kynurenine or 3-hydroxykynurenine which, having been formed peripherally, cross the blood-brain barrier to undergo final conversion to QUIN by brain kyn-3-OHase, kynureninase and 3-hydroxyanthranilate 3,4-dioxygenase (in contrast peripherally formed 3-hydroxyanthranilic acid enters the brain very poorly).

The optimal target for the design of inhibitors should be the rate limiting step through the pathway. Enzymatic studies in vitro on all the currently known enzymes along the two branches of the pathway have revealed that kyn-3-OHase, kynureninase and quinolinate phosphorybosiltransferase (see the kynurenine pathway) could contribute to determine the cerebral QUIN levels, though it is still unclear which of these enzymes is most effective in the normal brain and under pathological conditions. Studies on QUIN level, after administration to mice of different precursors (Erickson J. B., Flanagan E. M., Chang S. Y., Salter M. and Reinhard J. F. Jr. 1992. Soc. Neurosci. Abstr. 18: 442.) showed that brain and serum QUIN arise from qualitatively similar pathways. However, brain QUIN appears to be controlled heavily at the kyn-3-OHase step. As a consequence of these studies kyn-3-Ohase can be considered an important enzyme target for inhibition of QUIN biosynthesis.

Furthermore, being the first enzyme in the route of production of QUIN, the inhibition of kyn-3-OHase could lead to an accumulation of KYNA, the neuroprotectant metabolite of the pathway.

KYNA is an effective excitatory amino acid receptor antagonist with a particularly high affinity to the glycine modulatory site. (J. Neurochem., 52, 1319–1328, 1989). As a naturally occurring brain metabolite (J. Neurochem., 51, 177–180, 1988 and Brain Res., 454, 164–169, 1988), KYNA probably serves as a negative endogenous modulator of cerebral glutamatergic function (Ann. N.Y. Acad. Sci., 11, 290–296,1990); while applied directly into the brain, it exhibits anticonvulsant and neuroprotective properties (Neurosci. Lett. 48: 273–278. 1984).

In confirmation of all these data kyn-3-OHase inhibitors have recently been successfully applied to demonstrate for the first time, in the rat brain in vivo, the functional interdependence of the two branches of the kynurenine pathway by shifting cerebral metabolism towards an enhanced production of KYNA (Neuroscience 61: 237–244. 1994; Soc. Neurosci. Abstr. 21, 436.3. 1995).

In particular, systemic administration of the new and potent kyn-3-OHase inhibitor (R,S)-3,4-dichlorobenzoylalanine (FCE 28833) (see also Example 3b) causes a dose-dependent elevation in endogenous kynurenine and KYNA levels in rat brain tissue (Speciale et al. Eur. J. of Pharmacology, vol. 315, p.263–267, 1996).

These chemicals clearly hold great promise as research tools and may also harbor therapeutic potential since a decrease in brain QUIN and a concomitant increase in brain KYNA could be clinically desirable.

Moreover variants of the kyn-3-OHase enzyme could be present in different tissues and organs, and may constitute a possible target to develop more specific drugs.

In this perspective it is fundamental to clone the gene encoding for kyn-3-OHase, so that the protein can be studied from a molecular point of view and the recombinant enzyme can be obtained in reasonable quantity for further studies.

The purification of the enzyme and at least the partial sequence of the protein are the first steps to design degenerate oligonucleotides and to proceed with the cloning of the gene in a conventional hybridization way.

In 1975 Nisimoto et al. described the isolation of kyn-3-OHase from the mitochondrial outer membrane of rat liver in a 5 steps purification procedure (Nisimoto Y., Takeuchi F. and Shibata Y. 1975. J. Biochem. 78: 573–581). They described the isolation of a single homogeneus protein with a molecular weight of 200,000 Da and an isoelectric point of pH 5.4. The purified enzyme had a specific activity of 140 nmol min$^{-1}$ mg$^{-1}$ and an overall yield of 0.04%. In 1979, the same authors reported a 3 steps purification procedure with a better overall yield but a lower specific activity (Nisimoto et al. J. of Chromatography 169: 357–364. 1979).

More recently any attempts to reproduce these results, also from our biochemistry laboratories, have been unsuccessful; this is probably due to an instability of the enzyme during purification that do not allow a further analysis of its amino acidic sequence, thus precluding the possibility to adopt a conventional cloning approach.

Therefore, there is the need to set up an alternative cloning procedure and the invention aims to achieve this goal. According to the invention the problem is solved through the functional expression cloning in *Xenopus laevis* oocytes; this method is particularly useful to overcome the inconveniences deriving from the isolation of the protein by biochemical methods.

The functional expression cloning was first pioneered by Noma et al. (Noma Y., Sideras P., Naito T., Bergstedt-Lindquist S., Azuma C., Severinson E., Tanabe T., Kinashui T., Matsuda P., Yaoita Y. and Honjo T. 1986. Nature 319: 640–646.) and has been rapidly applied to the cloning of several plasma membrane proteins.

The strategy of functional expression cloning can be summarised as follow: functional expression, obtained with total mRNA from a given source, confirms the presence of mRNA coding for the protein of interest. The mRNA can then be fractionated according to size, the active fraction identified, and, after reverse transcription, used for the generation of a cDNA library. This library is then transcribed into polyadenylated cRNA, capped and expressed in the Xenopus oocytes. Subsequent appearance of the function in the oocytes confirms the presence of a full length clone (or at least a consistent functional part of it) in the library.

Functional expression cloning has the advantage over classical strategies in that the danger of sequencing "false positive" clones, due to cross reactivity of antibodies or nucleotide probes, can be avoided. Furthermore, most of the times full-length clones will directly be obtained (Sigel E. 1990. J. Membrane Biol. 117: 201–221).

Once cloned, the kyn-3-OHase cDNA obtained from a given source can be used to prepare probes for the screening of libraries derived from a different organisms. In this way, the expert in the art will recognize that, on the basis of the information provided herein, enzymes homologous to the ones specifically disclosed herein can be readily identified.

SUMMARY OF THE INVENTION

The present invention discloses the functional expression-cloning of rat kynurenine-3-hydroxylase and the molecular cloning of human kynurenine-3-hydroxylase.

In a first aspect, the present invention provides an isolated single or double stranded polynucleotide, typically DNA, having a nucleotide sequence which comprises a nucleotide sequence selected from the group consisting of: (a) the sense sequence of SEQ ID NO. 1 from about nucleotide position 45 to about nucleotide position 1481; the sense sequence of SEQ ID NO. 3 from about nucleotide position 34 to about nucleotide position 1494; (b) sequences complementary to the sequence of (a); (c) sequences that, on expression, encode polypeptides encoded by the sequence of (a); (d) analogous sequences that hybridize under stringent conditions to the sequences of (a) and (b); and (e) sequences homologous to the sequences of (a) that, on expression, encode polypeptides having kynurenine-3-hydroxylase activity.

A preferred embodiment is a DNA molecule. In another embodiment, the polynucleotide is an RNA molecule.

In another aspect, a DNA molecule of the present invention is contained in an expression vector. The expression vector preferably further comprises an enhancer-promoter operatively linked to the polynucleotide. In a preferred embodiment, the DNA molecule in the vector is the sequence of SEQ ID NO. 1 from about nucleotide position 45 to about nucleotide position 1481. In another preferred embodiment the DNA molecule in the vector is the sequence of SEQ ID NO. 3 from about nucleotide position 34 to about nucleotide position 1494.

The present invention still further provides for a host cell transformed with an expression vector of this invention. The host may be a prokaryotic or a eukaryotic cell. Example of a preferred prokaryotic host cell is *E. coli*, whereas, among the eukaryotic cells, preferred hosts are yeast, insect or mammalian cells. *Xenopus laevis* oocytes transiently expressing the kyn-3-OHase enzyme are also part of the present invention.

In a still further aspect the invention provides an isolated and purified recombinant kyn-3-OHase which is coded for by a nucleotide sequence selected from the group consisting of: (a) the sense sequence of SEQ ID NO. 1 from about nucleotide position 45 to about nucleotide position 1481; the sense sequence of SEQ ID NO. 3 from about nucleotide position 34 to about nucleotide position 1494; (b) a sequence complementary to the sequence of (a); (c) a sequence that, on expression, encodes a polypeptide encoded by the sequence of (a); (d) analogous sequences that hybridize under stringent conditions to the sequences of (a) and (b); and (e) sequences homologous to the sequences of (a) that, on expression, encode polypeptides having kynurenine-3-hydroxylase activity.

Furthermore, the invention provides a recombinant process for the transient expression of kyn-3-OHase, which process comprises extracting total mRNA from the tissues of a mammalian organism; generating a cDNA expression library by reverse transcription of the said mRNA; obtaining RNA in vitro from the said cDNA library; injecting the RNA into Xenopus oocytes; measuring the enzymatic activity; dividing the said library into several pools; selecting the positive clone; linearizing the plasmid DNA extracted from the positive clone; synthesizing the cRNA from said DNA; injecting the said cRNA into *Xenopus laevis* oocytes thus obtaining expression of kyn-3-OHase enzyme.

BRIEF DESCRIPTION OF THE DRAWINGS

FIG. 1. Protein alignment between the deduced amino acid sequence of K3OH clone (SEQ ID NO:2) and the deduced amino acid sequence of YBJ8_YEAST (SEQ ID NO:9).

FIG. 3. In vitro translation of K3OH cRNA. Lane 1, K3OH clone; 2, negative control. Two translation products are present: the upper band (~55,000 kDa) corresponds to a protein with the predicted molecular weight, the lower (~30,000 kDa) could be a partial translation product, due to a second ATG codon in frame, partially recognised as starting codon.

FIG. 4. Nucleotide alignment between the common portion of the sequences (nucleotides 1–1628 of SEQ ID NO:3 and nucleotides 1–1650 of SEQ ID NO:5); of the two human K3OH clones obtained by screening of a human liver cDNA library.

Figure 2:
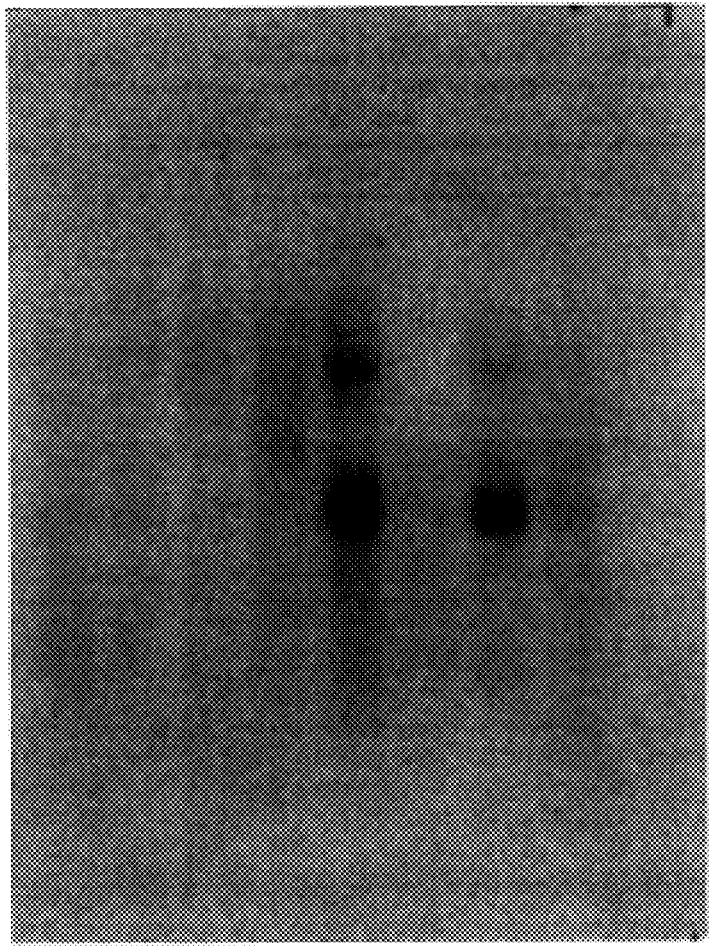
FIG. 2. Northern blot hybridization using K3OH cDNA as probe. Lane 1, heart; 2, brain; 3, spleen; 4, lung; 5, liver; 6, skeletal muscle; 7, kidney; 8, testis. mRNA species of 2 kb from rat liver, kidney and testis strongly hybridize with the K3OH probe; the signal obtained with testis is much less intense. In all the three tissues a 4.3 kb transcript which hybridize with K3OH probe is also present but the signal is less intense.

FIG. 5. Protein alignment between the deduced amino acid sequences of rat (SEQ ID NO:2) and human (SEQ ID NO:6) K3OH clones.

DETAILED DESCRIPTION OF THE INVENTION

The present invention provides isolated and purified polynucleotides that encode the enzyme kynurenine-3-hydroxylase (kyn-3-OHase), vectors containing these polynucleotides, host cells transformed with these vectors, a process of making the kyn-3-OHase using the above polynucleotides and vectors, and isolated and purified recombinant kyn-3-OHase.

For the purposes of the present invention as disclosed and claimed herein, the following is to be considered. The amino acid sequences are presented in the amino to carboxy direction, from left to right. The amino and carboxy groups are not presented in the sequence.

The nucleotide sequences are presented by single strand only, in the 5' to 3' direction, from left to right.

Nucleotides and amino acids are represented in the manner recommended by the IUPAC-IUB Biochemical Nomenclature Commission, or (for amino acids) by three letters code.

In one aspect, the present invention provides isolated and purified polynucleotides that encode the enzyme kyn-3-OHase from rat and human. A polynucleotide of the present invention is an isolated single or double stranded polynucleotide having a nucleotide sequence which comprises a nucleotide sequence selected from the group consisting of:

(a) the sense sequence of SEQ ID NO.1 from about nucleotide position 45 to about nucleotide position 1481; the sense sequence of SEQ ID NO. 3 from about nucleotide position 34 to about nucleotide position 1494;

(b) sequences complementary to the sequences of (a);

(c) a sequence that, on expression, encodes a polypeptide encoded by the sequences of (a);

(d) analogous sequences that hybridize under stringent conditions to the sequences of (a) and (b); and (e) sequences homologous to the sequences of (a) that, on expression, encode polypeptides having kynurenine-3-hydroxylase activity.

A preferred polynucleotide is a DNA molecule. In another embodiment, the polynucleotide is an RNA molecule.

The nucleotide sequence and deduced amino acid sequence of the rat kyn-3-OHase gene is set forth in SEQ ID NO. 1. The nucleotide sequences of human kyn-3-OHase clones are set forth in SEQ ID NO. 3 and SEQ ID NO. 5. The nucleotide sequences of SEQ ID NO. 1, SEQ ID NO. 3 and SEQ ID NO. 5 represent full length DNA clones of the sense strand of kyn-3-OHase genes and are intended to represent both the sense strand (shown on top) and its complementary strand.

The present invention also contemplates analogous DNA sequences which hybridize under stringent conditions to the DNA sequences set forth above. Stringent hybridization conditions are well known in the art and define a degree of sequence identity greater than about 80% preferably greater than 90%. The term "analogous" refers to those nucleotide sequences that encode analogous polypeptides, analogous polypeptides being those which have only conservative differences and which retain the conventional characteristics and activities of kyn-3-OHase. The present invention also contemplates naturally occurring allelic variations and mutations of the DNA sequences set forth above so long as those variations and mutations code, on expression, for a kyn-3-OHase enzyme.

Moreover, the invention contemplates homologous DNA sequences that, on expression, encode polypeptides having kynurenine-3-hydroxylase activity. As used herein, "homologous DNA sequences" are those sequences characterized by an homology, at the nucleotide level, greater than about 50%, preferably greater than about 60%, more preserably greater than about 70%, in at least one functional domain of the encoded polypeptide, with respect to the corresponding region of the sequences disclosed in the present invention. Homologous DNA sequences include those sequences coding for isoforms of the kynurenine-3-hydroxylase enzyme encoded by the the DNA sequences set forth above. Such isoforms can be expressed in different tissues of the same organism as a result, e.g., of alternative splicing or because coded for by other genes.

Homologous DNA sequences are also those sequences coding for a kyn-3-OHase of any species of origin. Preferably the DNA sequences code for enzymes of mammalian origin; more preferably the DNA sequences code for the human kyn-3-OHase enzyme.

As is well known in the art, because of the degeneracy of the genetic code, there are numerous other DNA and RNA molecules that can code for the same polypeptide as that encoded by the aforementioned kyn-3-OHase genes. The present invention, therefore, contemplates those other DNA and RNA molecules which, on expression, encode the polypeptides of SEQ ID NO. 2, 4 and 6.

Having identified the amino acid residue sequence encoded by a kyn-3-OHase gene, and with knowledge of all triplet codons for each particular amino acid residue, it is possible to describe all such encoding RNA and DNA sequences. DNA and RNA molecules other than those specifically disclosed herein characterized simply by a change in a codon for a particular amino acid, are within the scope of this invention.

A table of amino acids and their representative abbreviations, symbols and codons is set forth below in the following Table.

| Amino acid | Abbrev. | Symbol | Codon(s) |
| --- | --- | --- | --- |
| Alanine | Ala | A | GCA GCC GCG GCU |
| Cysteine | Cys | C | UGA UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

-continued

| Amino acid | Abbrev. | Symbol | Codon(s) |
|---|---|---|---|
| Valine | Val | V | GUA GUC GUG GUU |
| Tryptophan | Trp | W | UGG |
| Tyrosine | Tyr | Y | UAC UAU |

As is well known in the art, codons constitute triplet sequences of nucletotides in mRNA molecules and, as such, are characterized by the base uracil (U) in place of base thymidine (T) (which is present in DNA molecules).

A simple change in a codon for the same amino acid residue within a polynucleotide will not change the structure of the encoded polypeptide.

The kyn-3-OHase enzymes of the present invention include proteins homologous to, and having essentially the same biological properties as, the proteins coded for by the nucleotide sequence herein disclosed. This definition is intended to encompass isoforms and natural allelic variants of kyn-3-OHase sequences.

With the knowledge of the sequence information disclosed in the present invention, the expert in the art can identify and obtain DNA sequences which encode the kyn-3-OHase enzyme from different sources (i.e. different tissues or different organisms) through a variety of means well known to him and disclosed by, for example, Maniatis et al., Molecular cloning: a laboratory manual, Second Edition, Cold Spring Harbor Press, Cold Spring Harbor, N.Y. (1989).

For example DNA which encodes the kyn-3-OHase enzyme may be obtained by screening of mRNA, cDNA or genomic DNA with oligonucleotide probes generated from the kyn-3-OHase enzyme gene sequences information provided herein. Probes may be labeled with a detectable group such as a fluorescent group, a radioactive atom or a chemiluminescent group in accordance with known procedures and used in conventional hybridization assays, as described by, for example, Maniatis et al. Molecular cloning: a laboratory manual, Second Edition, Cold Spring Harbor Press, Cold Spring Harbor, N.Y. (1989).

Kyn-3-OHase gene sequence may alternatively be recovered by use of the polymerase chain reaction (PCR) procedure, with the PCR oligonucleotide primers produced from the kyn-3-OHase enzyme sequence provide herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template-dependent, polymerase mediated replication of a desired nucleic acid molecule.

The recombinant DNA molecules of the present invention can be produced through any of a variety of means well known to the experts in the art and disclosed by, for example, Maniatis et al. Molecular cloning: a laboratory manual, Second Edition, Cold Spring Harbor Press, Cold Spring Harbor, N.Y. (1989). Example 5 describes one of the possible procedures which can be followed for this purpose.

In order to replicate the kyn-3-OHase enzyme DNA sequence, this must be cloned in an appropriate vector. A vector is a replicable DNA construct.

Vectors are used herein either to amplify DNA encoding the kyn-3-Ohase enzyme and/or to express DNA which encodes the kyn-3-OHase enzyme. An expression vector is a replicable DNA construct in which a DNA sequence encoding kyn-3-OHase enzyme is operably linked to suitable control sequences capable of effecting the expression of the kyn-3-OHase enzyme in a suitable host. DNA regions are operably linked when they are functionally related to each other. For example: a promoter is operably linked to a coding sequence if it controls the transcription of the sequence. Amplification vectors do not require expression control domains. All that is needed is the ability to replicate in a host, usually conferred by an origin of replication, and a selection gene to facilitate recognition of transformants.

DNA sequences encoding kyn-3-OHase enzyme may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesiderable joining, and ligation with appropriate ligases. Techniques for such manipulation are disclosed by Maniatis et al. Molecular cloning: a laboratory manual, Second Edition, Cold Spring Harbor Press, Cold Spring Harbor, N.Y. (1989) and are well known in the art.

Expression of the cloned sequence occurs when the expression vector is introduced into an appropriate host cell. If a prokaryotic expression vector is employed, then the appropriate host cell would be any prokaryotic cell capable of expressing the cloned sequences, for example E. coli. Similarly, if an eukaryotic expression vector is employed, then the appropriate host cell would be any eukaryotic cell capable of expressing the cloned sequence. A yeast host may be employed, for example S. cerevisiae. Alternatively, insect cells may be used, in which case a baculovirus vector system may be appropriate. Another alternative host is a mammalian cell line, for example COS-1 cells.

The need for control sequences into the expression vector will vary depending upon the host selected and the transformation method chosen. Generally, control sequences include a transcriptional promoter, an optional operator sequence to control transcription, a sequence encoding suitable mRNA ribosomal binding, and sequences which control the termination of transcription and translation. Vectors useful for practicing the present invention include plasmids, viruses (including phages), retroviruses, and integrable DNA fragments (i. e. fragments integrable into the host genome by homologous recombination). The vectors replicate and function independently of the host genome, or may, in some instances, integrate into the genome itself.

Expression vectors should contain a promoter which is recognized by the host organism. The promoter sequences of the present invention may be either prokaryotic, eukaryotic or viral. Example of suitable prokaryotic sequences include the $P_{R\ and\ PL}$ promoters of bacteriophage lambda (The bacteriophage Lambda, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980) ); the trp, recA, heat shock, and lacZ promoters of E. Coli and the SV40 early promoter (Benoist, C. et al. nature 290: 304–310 (1981)).

As far as the Shine Dalgarno sequence is concerned, preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding kyn-3-OHase and result in the expression of the mature kyn-3-OHase protein.

Alternatively, the DNA encoding kyn-3-OHase may be preceded by a DNA sequence encoding a carrier peptide sequence. In this case, a fusion protein is produced in which the N-terminus of kyn-3-OHase is fused to a carrier peptide, which may help to increase the protein expression levels and intracellular stability, and provide simple means of purification A preferred carrier peptide includes one or more of the IgG binding domains of protein A are easily purified to homogeneity by affinity chromatography e. g. on IgG-coupled Sepharose. Alternatively, many vectors have the advantage of carrying a stretch of histidine residues that can be expressed at the N-terminal or C-terminal end of the target protein. Thus the protein of interest can be recovered by metal chelation chromatography (see the method described herein below under Example 5). A DNA sequence encoding a recognition site for a proteolytic enzyme such as enterokinase, factor X, procollagenase or thrombin may immediately precede the sequence for kyn-3-OHase to permit cleavage of the fusion protein to obtain the mature kyn-3-OHase protein.

Moreover, a suitable expression vector includes an appropriate marker which allows the screening of the transformed host cells. The transformation of the selected host is carried out using any one of the various techniques well known to the expert in the art and described in Maniatis et al. Molecular cloning: a laboratory manual, Second Edition, Cold Spring Harbor Press, Cold Spring Harbor, N.Y. (1989).

One further embodiment of the invention is a prokaryotic host cell transformed with the said expression vector and able to produce, under appropriate culture conditions, the kyn-3-OHase of the invention.

A peculiar example of expression in eukaryotic cells is represented by *Xenopus laevis* oocytes. This system has also been used as a strategy to clone the DNA sequence of the present invention.

In this case the vector, which is not used to transform the cell, is linearized with an appropriate restriction enzyme and used for in vitro synthesis of cRNA, including capping, using RNA polymerase. Techniques for such manipulation are well known in the art; see for example Maniatis et al. Molecular cloning: a laboratory manual, Second Edition, Cold Spring Harbor Press, Cold Spring Harbor, N.Y. (1989). The cRNA is then injected into the oocytes according to the procedure described herein under Example 1. These cells are capable of transiently expressing the functional enzyme and can be used to study the characteristics of variants of kyn-3-OHase and to test new compounds.

Moreover, cultures of cells derived from multicellular organisms are a desiderable host for recombinant kyn-3-OHase synthesis. In principal, any eukaryotic cell culture is workable, whether from vertebrate or invertebrate culture, including insect and mammalian cells. Propagation of such cells in cell culture has become a routine procedure. See Tissue Culture, Academic Press, Kruse and Patterson, eds. (1973). Examples of useful host cell lines are HeLa cells, CHO and COS cell lines. The transcriptional and translational control sequences in expression vectors to be used in transforming vertebrate and invertebrate cells are often provided by viral sources, for example, commonly used promoters are derived from Adenovirus 2, polyoma and SV40. See, e. g. U.S. Pat. No. 4,599, 308.

An origin of replication may be provided either by construction of the vector to include an exogenous origin or may be provided by the host cell chromosomal replication mechanism. If the vector is integrated into the host cell chromosome, the latter may be sufficient.

Rather than using vectors which contains viral origins of replication, one can transform mammalian cells by the method of cotransformation with a selectable marker and kyn-3-OHase DNA. An example of a suitable marker is dihydrofolate reductase (DHFR) or thymidine kinase. See U.S. Pat. No. 4,399,216.

Cloned genes and vectors of the present invention are useful to transform cells which do not ordinarly express kyn-3-OHase to thereafter express this enzyme. Such cells are useful as intermediates for making recombinant kyn-3-OHase preparations useful for drug screening.

Furthermore, structural data deriving from the analysis of the deduced amino acid sequences of the DNAs of the present invention are useful to design new drugs, more specific and therefore with a higher pharmacological potency.

Sequence comparison of the two clones obtained by screening of the human liver cDNA library (SEQ ID NO. 3 and SEQ ID NO. 5) revealed 100% nucleotide homology in the coding region (FIG. 4) Notably, the cloned sequence in SEQ ID NO. 5 shows a huge 3' untraslated region that could contain regulatory elements and need further investigations.

Comparison between the deduced amino acid sequences of the rat Kyn3OHase (SEQ ID NO. 2) and the human Kyn3OHase (SEQ ID NOs. 2 and 6) showed 73% of identity (FIG. 5).

Comparison of the DNA sequences of the present invention with the sequences present in all the available data bases showed a significant homology with a portion of the *Saccharomyces cerevisiae* genomic DNA (YBJ8_YEAST) (SEQ ID NO:9). This is a region containing a putative open reading frame of 1380 nucleotides corresponding to a hypothetical protein whose identity and function are so far unknown. FIG. 1 shows the protein alignment between rat Kyn3OHase (SEQ ID NO:2) and YBJ8_YEAST (SEQ ID NO:9), the two deduced amino acid sequences show 35% of homology. Rat Kyn3OHase and therefore human Kyn3OHase are also homologous to p-hydroxybenzoate hydroxylase, a flavoprotein whose crystal structure has been resolved (Schreuder, H. A., et al. 1988, J. Mol. Biol. 199, 637–648). The homology between these proteins resulted to be highly significant in the regions containing the putative binding sites for FAD and NADP. Computer modelling could be therefore used to develop a putative tertiary structure of Kyn-3-OHase based on the available information on p-hydroxybenzoate hydroxylase. This approach can help in designing novel enzyme inhibitor based on the predicted structure of Kyn-3-OHase.

Variants of the kyn-3-OHase enzymes of the present invention (obtained as described above) could be present in different tissues and/or organs, and might represent potential new pharmacological targets to develop more specific drugs.

Cloned genes of the present invention, and oligonucleotides derived therefrom, are useful for screening for restriction fragment length polymorphism (RFLP) associated with certain disorders.

Oligonucleotides derived from the kyn-3-OHase DNA sequences of the present invention are useful as diagnostic tools for probing kyn-3-OHase gene expression in various tissues. For example, tissue can be probed in situ with oligonucleotide probes carrying detectable groups by conventional autoradiography techniques to investigate native expression of this enzyme or pathological conditions relating thereto.

The present invention is explained in greater detail in the following examples. These examples are intended to be illustrative of the present invention, and should not be constructed as limiting thereof.

EXAMPLE 1

Expression-cloning in *Xenopus laevis* oocytes a) Preparation of *Xenopus laevis* oocytes Ovarian tissue was dissected from adult female *Xenopus laevis*: a small incision was made in the skin and body wall in the posterior ventral side of the animal. The ovary consists of several lobes that were snipped off using scissors and placed in colture medium (ND solution: 5 mM hepes-NaOH, pH 7.6, 96 mM NaCl, 2 mM KCl, 1 mM $MgCl_2$). The incision in the body wall was then sutured separately from the skin, which subsequently was sutured as well, and the animal was left to recover in shallow water (L. D. Smith et al. 1991. Methods in Cell Biol. 36: 45–60).

Each oocyte is closely surrounded by about 5,000 follicle cells, which greatly affect the composition and synthesis of ovarian material unless removed.

Individual oocytes of stages were obtained by gentle agitation in ND solution plus 1–2mg/ml collagenase for 60–90 min. They were then maintained at 18° C. in ND solution enriched with 1.8 mM $CaCl_2$ and 20 mg/l gentamycin. Oocytes of stages 5 and 6 were injected 24 hours later with 50 nl RNA or water (N. Dascal and I. Lotan 1992. Methods in Mol. Biol. 13: 205–225).

b) mRNA isolation and injection

The injected mRNA was poly(A)* RNA isolated from rat heart and kidney.

Rat kidneys and hearts were removed and frozen in liquid nitrogen. Total RNA was isolated with a guanidine thiocyanate extraction followed by $CsCl_2$ gradient centrifugation (Maniatis et al. Molecular cloning: a laboratory manual, Second Edition, Cold Spring Harbor Press, Cold Spring Harbor, N.Y. (1989). mRNA was isolated by oligo-dT chromatography (Pharmacia Biotech, Uppsala, Sweeden).

Oocytes were injected with a Drummond Nanoject microdispenser. To avoid accidental injection into the nucleus, the needle was inserted close to the equator or in the vegetal (light) half of the oocytes. 1–3 days after injection the oocytes were assayed for kyn-3-OHase.

c) Rat Kyn-3-OHase activity expressed in *X. laevis* oocytes: biochemical assay.

Kyn-3-OHase activity was quantified by the conversion of L-kyn to 3-OH-Kyn. Oocytes were sonicated in ice-cold 0.14 M KCl/20 mM potassium phosphate buffer (pH 7.0) to obtain a final protein concentration of 5–10 mg/ml. The reaction mixture consisted of 100 ml of oocytes homogenates and 100 ml of 100 mM potassium phosphate buffer containing 4 mM $MgCl_2$, 0.8 mM NADPH and different concentrations of L-kyn. After 1 h incubation at 37° C. the reaction was terminated by adding 200 ml of 1M percloric acid (Saito K. et al., J. Neurochem. 1993. 60:180). 3-OH-Kyn was quantified by HPLC coupled to a coulometric detector (+0.2V), (Heyes M. P. and Querry B. J. J. Chrom. 1994. 428: 340).

d) Construction of a rat kidney cDNA expression library

A directional cDNA library was constructed by using size-selected rat kidney poly(A)$^+$RNA that had been shown to induce expression of kyn-3-OHase activity in the oocytes. The cDNA library was constructed by using a commercial kit (SuperScript plasmid system, pSPORT1 vector; GIBCO/BRL) and precisely following the suppliers instructions. The library contained about $5 \times 10^4$ colonies, initial pools for screening contained about 2000 colonies.

e) Library screening

Plasmid DNA was isolated by standard procedures (alkaline lysis followed by a purification on Qiagen resin; Kontron Zürich). Plasmids were linearized with Not I and used for in vitro synthesis and capping of cRNA using T7 RNA polymerase (Stratagene) and following the supplier's instructions. Initially the library was divided into 25 pools of ~2000 colonies; cRNA obtained transcribing the insert of each pool of colonies was injected in the oocytes and screened for the expressed kyn-3-Ohase activity (See Example 1c for the methods). The positive pool identified for its kyn-3-OHase expressed activity (175 pmoles/h/mg protein: about 30 fold higher than that induced by the injection of total kidney poly (A)$^+$RNA) was then split into several sub-pools and assayed with the same procedure. Following the same criterion, in the last round of screening we had a single positive clone showing an activity of 3747 pmoles/h/mg protein (about 400 fold higher than that induced by injection of total rat kidney poly(A)$^+$RNA).

EXAMPLE 2

Characterization of the cDNA encoding rat kyn-3-OHase.

a) DNA sequencing

Both strands of the cDNA were sequenced. Sequencing was carried out with universal and forward primers and subsequently with a series of synthetic oligonucleotide primers according to the dideoxy chain termination method (F. Sanger et al: Proc. Natl. Acad. Sci. USA. 1977. 74: 5463–5467) using Sequenase (United States Biochemicals Corp., Cleveland, Ohio).

The sequenced cDNA, depicted in SEQ ID NO. 1, encodes a deduced protein of 478 amino acid residues (the predicted amino acid sequence is shown in SEQ ID NO. 2). Using the protein algorithm described by Gavel and Von Heijne (Protein Engineering, 4, 33–37, 1990) a potential mitochondrial signal peptide is predicted in position 1 to 31 of the deduced protein.

b) Northern analysis

A commercial premade Northern blot of poly(A)$^4$ RNA from different rat tissues was used (CLONTECH laboratories, USA). A full length cDNA probe of the clone was labeled by random priming (Amersham) using [a-$^{32}$P] dCTP (DuPont/NEN). Blot was prehybridized and hybridized in a buffer containing 50% (vol/vol) formamide 5× standard saline citrate (SSC: 750 mM NaCl, 75 mM sodium citrate), 1× Denhardt's solution, salmon sperm at 0.25 mg/ml, 1 SDS overnight at 42° C. After hybridization, blot was washed three times in 2× SSC/0.1% SDS at 42° C. (FIG. 2).

c) In vitro translation

In vitro translation of the rat Kyn-3-OHase CRNA was performed with a rabbit reticulocyte lysate system (Promega) following the supplier's instructions.

Radiolabeled proteins synthesized in vitro using [3, 4, 5-$^3$H] L-leucine were resolved by denaturing polyacrylamide gel electrophoresis (SDS-PAGE) and detected by autoradiography (FIG. 5) (Maniatis et al. 1989. Molecular cloning: a laboratory manual, Second Edition, Cold Spring Harbor Press, Cold Spring Harbor, N.Y.)

EXAMPLE 3

Biochemical characterization of rat kyn-3-OHase expressed in *Xenopus l.* oocytes.

*Xenopus l.* oocytes were first injected with 25 ng of poly(A)$^+$RNA isolated from rat kidney. Three days after the injection, oocytes homogenate showed the production of 6.3 pmoles/h/mg protein of 3-OH-kyn after 1 hour incubation at 37° C. in the presence of 1 mM L-kyn. The production of 3-OH-kyn in water-injected oocytes and in oocytes injected with poly(A)$^+$RNA isolated from rat heart, a tissue in which the activity of the enzyme is known to be very low (E. Okuno and R. Kido "Kynurenine and Serotonin pathways" Ed. by Schwarcz et al., Plenum Press, New York, 1991), was at the detection limit of the method and was similar to that observed in non-injected oocytes.

a) cRNA dose-response in Xenopus 1. oocytes

Increasing doses (range 0.1–25 ng) of cRNA, obtained from the positive clone, were injected into oocytes which were then tested for kyn-3-OHase activity in the presence of 100 mM of L-kyn. A linear dose-dependent effect was observed up to 5 ng cRNA/oocyte. At this dose the kyn-3-OHase activity was 35.7 nmoles/h/mg protein. No further increase of the activity was measured when higher cRNA doses were injected.

b) Effect of a selective kyn-3-OHase inhibitor FCE 28833A on the expressed enzyme activity.

An inhibition experiment was performed using FCE 28833A, a well known Kyn-3-OHase inhibitor (Molinari, A., M. Cini, M. Marconi, H. -Q. Wu, R. Schwarcz, A. Bonsignori, R. A. McArthur, M. Varasi and C. Speciale, 1995, Soc. Neurosci. Abstr. 21, 436.3).

Oocytes injected with the kynOH clone were homogenized and incubated in the presence of 50 $\mu$M L-kyn and different concentrations of FCE 28833A. In this experimental condition the $IC_{50}$ of the inhibitor was 0.29 $\mu$M, this is in agreement with the previous results obtained in rat brain mithocondria (Molinari, A., M. Cini, M. Marconi, H. -Q. Wu, R. Schwarcz, A. Bonsignori, R. A. McArthur, M. Varasi and C. Speciale, 1995, Soc. Neurosci. Abstr. 21, 436.3).

EXAMPLE 4

Molecular cloning of human Kyn-3-OHase a) cDNA library screening

About 1,000,000 recombinant phages of a λ ZapII human liver cDNA library (Stratagene) were plated on a lawn of *E. coli* XL1 Blue cells. After an overnight growth at 37° C. the recombinant phages were transferred in duplicate on nitrocellulose filters, their DNA was denatured, neutralized and baked under vacuum at 80° C. for 2 h. Prehybridization and hybridization were carried out under stringent conditions (6× SSC, 5× Denhardt, 0,1%SDS and Salmon sperm 100 $\mu$g/ml at 65° C.). The probe used was the MluI-HindIII 668 bp fragment obtained from the rat Kyn-3-OHase cDNA (K3OH). The probe was gel-purified by Qiaex (Qiagen) and labeled with $^{32}$P by Multiprime DNA labeling system (Amersham).

The filters were washed at 65° C. three times in 2× SSC, 0.1% SDS and once in 1× SSC, 0.05% SDS. Filters were exposed to Kodak X-AR film (Eastman Kodak Company, Rochester, N.Y., USA) with intensifying screen at −80° C.

Positive phage plaques were isolated and screened again twice in order to isolate single clones.

b) Recombinant phage DNA extraction and Sequencing methods

*E. coli* XL1 Blue cells were coinfected with about $10^5$ phage particles corresponding to the positive clone selected and 1 $\mu$l of EX Assist helper phage ($10^6$ pfu/$\mu$l; Stratagene) The mixture was incubated at 37° C. for 15 min and later incubated with 3 ml of LB medium for 3 h. Cells were spinned down and the supernatant was heated at 70° C. for 15 min. SORL cells at $OD_{600}$=1 were mixed with the supernatant containing the phagemid pBluescript, incubated for 15 min at 37° C. and plated on LB-ampicilline (50 $\mu$g/ml) plates. Single clones were incubated overnight in LB-ampicilline and DNA was extracted according to the instructions of Qiagen Plasmid Maxi Protocol. Both strands of the cDNA were sequenced. Sequencing was carried out with universal and forward primers and subsequently with a series of synthetic oligonucleotide primers according to the dideoxy chain termination method (F. Sanger et al: Proc. Natl. Acad. Sci. USA. 1977. 74: 5463–5467) using Sequenase (United States Biochemicals Corp., Cleveland, Ohio). Eight positive clones were isolated and characterized by restriction analysis, to obtain the size of insert. All the positive clones were then sequenced on both strands: seven clones had an insert of 1628 bp, depicted in SEQ ID NO. 3, while one had a bigger insert, of 5000 bp depicted in SEQ ID NO. 5 All the eight clones contained an identical (100% nucleotide level) open reading frame of 1458 bp encoding a deduced protein of 486 amino acid residues (the predicted amino acid sequence is shown in SEQ ID NO. 4 and 6). The biggest clone had a huge 3' untraslated region (see FIG. 4). Sequence comparison between the deduced amino acid sequences of the human K3OH (SEQ ID NO. 4 and SEQ ID NO. 6) and the rat Kyn3OHase (SEQ ID NO. 2) showed 73% of identity (FIG. 5).

Also in this case, as for the rat protein, using the protein algorithm described by Gavel and Von Heijne (Protein Engineering, 4, 33–37, 1990) a potential mitochondrial signal peptide is predicted in position 1 to 31 of the deduced protein.

EXAMPLE 5

Inducible expression in *Escherichia coli* a) Construction of the vector

The expression plasmid encoding human Kyn3OHase was constructed as follows:

a) PCR amplification was used to isolate the translated portion of the human Kyn3OHase cDNA sequence, to add the convenient restriction enzyme sites and to place the coding region in the proper reading frame. Two specific oligonucleotides were designed: the sense orientation oligonucleotide (5'-CAGGAATTCCATATGGACTCATCTGTC-3') (SEQ ID NO. 7)contains the Nde I restriction site that reconstitutes the ATG codon and therefore place the cDNA in frame; the antisense-orientation oligonucleotide (5'-CGGGATCCCGCTATCACCTGCTAATGA-3') (SEQ ID NO. 8) contains the BamH I restriction site and complements the sequence from the end of the coding region. In both the oligonucleotides the restriction site is flanked by a "spacer" at the 5' end to allow for efficient digestion.

b) The Nde I/BamH I digested fragment, after being controlled by sequencing, was ligated into the vector pET-11a (Novagen, USA) cut with the same restriction enzymes and dephosphorylated.

c) Initial cloning was done in DH5α strain to allow the examination of the construct sequence by restriction analysis.

b) Transformation and induction of BL21(DE3)pLysS strain

After positive clones were identified, the plasmid was isolated (Easy-pure plasmid preps, Primm Labs, Italy) and used for transformation into BL21(DE3) pLysS according to the instructions of Novagen, USA.

After the target plasmid was established in the expression host, expression of the human K3OH DNA was induced by addition of IPTG to a growing culture.

Following an induction protocol suggested by Novagen, a single colony or a few $\mu$l from a glycerol stock were grown into 2 ml LB medium containing the appropriate antibiotic at 37° C. until the $OD_{600}$ reached 0.6–1. The culture was stored at 4° C. overnight. The cells were then collected by centrifugation, resuspended in 2 ml fresh medium+ antibiotics and used to inoculate 100 ml medium+ antibiotics.

The culture was incubated with shaking at 37° C. until $OD_{600}$ reached 0.4–1. Samples for the uninduced control were removed and IPTG was added to a final concentration of 0.1–1 mM.

Induction time was 2–5 hours. Some induction experiments were performed at 30° C. overnight.

The cells were harvested by centrifugation at 3000 rpm for 10 min at 4° C., resuspended in 0.25 culture volume of cold 50 mM Tris-HCl pH 8.0, 2 mM EDTA and centrifuged as above. After removal of the supernatant, the cells were stored as frozen pellets at −70° C.

c) Recombinant Kyn-3-OHase activity: biochemical assay.

Kyn-3-OHase activity was quantified by the conversion of L-kyn to 3-OH-Kyn. *E. coli* pellets were resuspended in ice-cold 0.14 M KCl/20 mM potassium phosphate buffer (pH 7.0) to obtain a final protein concentration of 1–3 mg/ml and sonicated. The reaction mixture consisted of 100 μl of cells homogenates and 100 ml of 100 mM potassium phosphate buffer (pH 7.5) containing 4 mM $MgCl_2$, 0.8 mM NADPH and increasing concentrations of L-kyn. After 1 h incubation at 37° C. the reaction was terminated by adding 200 ml of 1M percloric acid (Saito K. et al., J. Neurochem. 1993. 60:180). 3-OH-Kyn was quantified by HPLC coupled to a coulometric detector (+0.2V), (Heyes M. P. and Querry B. J. J. Chrom. 1994. 428: 340)

EXAMPLE 6
Biochemical characterization of human recombinant kyn-3-OHase expressed in *E. coli*

Recombinant kyn-3-OHase activity measured in cells grown at 37° C. until the $OD_{600}$ reached 0.6, induced for 2 hours at 37° C. adding 1 mM IPTG was about 10 nmol/h·mg protein, enzymatic activity of uninduced cells in the same conditions was less than 5% (homogenates incubated for 1 hour at 37° C. with 500 μM L-kyn; see Example 5c). Not transformed cells did not show any kyn-3-OHase activity.

a) Kinetic analysis of human recombinant kyn-3-OHase

To further characterize human recombinant K3OH activity, a kinetic study was performed by incubating *E. coli* extracts with increasing concentrations of L-kynurenine, ranging from 1 to 4,000 μM (Induction conditions: $OD_{600}$= 0.6, [IPTG]=1 mM, 2 h at 37° C.).

The kinetic parameters: $K_m$ and $V_{app}$ (apparent maximal rate) measured in these conditions and calculated using the fitting curve analysis of Sigma Plot programme were 57±2 μM and 10.5±0.11 nmol/hour.mg of protein, respectively.

The Km value is in the same order of magnitude of that measured in rat liver homogenate.

b) Effect of a selective kyn-3-OHase inhibitor FCE 28833A on the recombinant enzyme activity.

An inhibition experiment was performed using FCE 28833A, a well known Kyn-3-OHase inhibitor (Speciale C., Wu H. -Q., Cini M., Marconi M., Varasi M. and Schwarcz R. 1996, Eur. J. of Pharmacol. 315: 263–267)

*E. coli* extracts were incubated in the presence of 50 μM L-kyn and different concentrations of FCE 28833A. In this experimental condition the $IC_{50}$ of the inhibitor was 0.2±0.06 μM , this is in agreement with the previous results obtained in rat brain mitochondria (Speciale C., Wu H. -Q., Cini M., Marconi M., Varasi M. and Schwarcz R. 1996, Eur. J. of Pharmacol. 315: 263–267).

EXAMPLE 7
Recombinant expression of a fusion K3OH protein with a cleavable His.Tag sequence for rapid affinity purification The plasmid pET-15b (Novagen, USA) was used. This vector has the advantage of carrying the His.Tag sequence, a stretch of 6 consecutive histidine residues that can be expressed at the N-terminal of the target protein. The His.Tag sequence binds to divalent cations immobilized on a metal chelation resin. After unbound proteins are washed away, the target protein can be recovered by elution with imidazole.

The pET-15b construct expressing human K301 was constructed as follows: the insert contained in plasmid pET-11a (See Example 5) was excided by digestion with Nde I/BamH I and ligated into the vector pET-15b cut with the same restriction enzymes and dephosphorylated.

Initial cloning was done in DH5α strain to allow the examination of the construct sequence by restriction analysis. After positive clones were identified, the plasmid was isolated (Easy-pure plasmid preps, Primm Labs, Italy) and used for transformation into BL21(DE3) pLysS according to the instructions of Novagen, USA.

After the target plasmid was established in the expression host, expression of the human K3OH DNA was induced by addition of IPTG to a growing culture. Induction conditions were the same used in Example 5.

---

What is claimed is:

1. An isolated polynucleotide comprising SEQ ID NO: 1.

2. An isolated polynucleotide comprising nucleotides 45 to 1481 of SEQ ID NO:1.

3. An isolated polynucleotide, wherein said polynucleotide is complementary to the isolated polynucleotide of claim 1.

4. An isolated polynucleotide which hybridizes under stringent conditions to the polynucleotide of claim 1.

5. A polypeptide comprising SEQ ID NO:2.

6. A polynucleotide which encodes the polypeptide of claim 5.

7. The polynucleotide of claim 6, consisting of nucleotides 45 to 1481 of SEQ ID NO:1.

8. A vector comprising the polynucleotide of claim 1.

9. The vector of claim 8, wherein said vector is a plasmid or a virus.

10. A host cell comprising the polynucleotide of claim 1.

11. The host cell of claim 10 wherein said host cell is selected from the group consisting of a bacterial cell, a yeast cell, an insect cell, and a mammalian cell.

12. A method of transiently expressing a polypeptide comprising SEQ ID NO:2, which process comprises extracting total mRNA from the tissues of a mammalian organism;

generating a cDNA expression library by reverse transcription of said mRNA;

obtaining RNA in vitro from said cDNA library;

injecting the RNA into Xenopus oocytes;

measuring the enzymatic activity;

dividing said library into several pools;

selecting a positive clone containing the polynucleotide of claim 6;

linearizing the plasmid DNA extracted from the positive clone;

synthesizing the cRNA from said DNA; and injecting said cRNA into *Xenopus laevis* oocytes.

13. An isolated polynucleotide comprising SEQ ID NO:3.

14. An isolated polynucleotide comprising nucleotides 34 to 1494 of SEQ ID NO:3.

15. An isolated polynucleotide, wherein said polynucleotide is complementary to the isolated polynucleotide of claim 13.

16. An isolated polynucleotide which hybridizes under stringent conditions to the polynucleotide of claim 13.

17. A polypeptide comprising SEQ ID NO:4.

18. A polynucleotide which encodes the polypeptide of claim 17.

19. The polynucleotide of claim 18, consisting of nucleotides 34 to 1494 of SEQ ID NO:3.

20. A vector comprising the polynucleotide of claim 13.

21. The vector of claim 20, wherein said vector is a plasmid or a virus.

22. A host cell comprising the polynucleotide of claim 13.

23. The host cell of claim 22, wherein said host cell is selected from the group consisting of a bacterial cell, a yeast cell, an insect cell, and a mammalian cell.

24. A method of transiently expressing a polypeptide comprising SEQ ID NO: 4, comprising:

extracting total mRNA from the tissues of a mammalian organism;

generating a cDNA expression library by reverse transcription of said mRNA;

obtaining RNA in vitro from said cDNA library;

injecting the RNA into Xenopus oocytes;

measuring the enzymatic activity;

dividing said library into several pools;

selecting a positive clone containing the polynucleotide of claim 18;

linearizing the plasmid DNA extracted from the positive clone;

synthesizing the cRNA from said DNA; and injecting said cRNA into *Xenopus laevis* oocytes.

* * * * *